(12) United States Patent
Boyer, II et al.

(10) Patent No.: US 6,767,369 B2
(45) Date of Patent: Jul. 27, 2004

(54) PLUGS FOR FILLING BONY DEFECTS

(75) Inventors: Michael L. Boyer, II, Paoli, PA (US);
David C. Paul, Phoenixville, PA (US);
Thomas B. Higgins, Berwyn, PA (US);
Christopher M. Angelucci,
Schwenksville, PA (US); Dominique D. Messerli, West Chester, PA (US);
Kenneth I. Kobayashi, Exton, PA (US)

(73) Assignee: Synthes (USA), Paoli, PA (US)

( * ) Notice: Subject to any disclaimer, the term of this patent is extended or adjusted under 35 U.S.C. 154(b) by 123 days.

(21) Appl. No.: 09/814,223

(22) Filed: Mar. 22, 2001

(65) Prior Publication Data

US 2001/0039457 A1 Nov. 8, 2001

Related U.S. Application Data

(60) Provisional application No. 60/191,099, filed on Mar. 22, 2000.

(51) Int. Cl.⁷ .................................. A61F 2/28
(52) U.S. Cl. .................................. 623/23.63
(58) Field of Search ............. 623/17.11, 23.48, 623/17.12, 17.16, 16.11, 23.63; 606/61, 71

(56) References Cited

U.S. PATENT DOCUMENTS

| | | | |
|---|---|---|---|
| 4,011,602 A | 3/1977 | Rybicki et al. ............. 3/1.9 |
| 4,501,269 A | 2/1985 | Bagby ....................... 128/92 G |
| 4,745,914 A | 5/1988 | Frey et al. ................ 128/92 VP |
| 4,834,757 A | 5/1989 | Brantigan .................. 623/17 |
| 4,877,020 A | 10/1989 | Vich .......................... 128/92 V |
| 4,936,851 A | 6/1990 | Fox et al. .................. 623/16 |
| 4,950,296 A | 8/1990 | McIntyre .................... 623/16 |
| 4,961,740 A | 10/1990 | Ray et al. .................. 606/61 |
| 5,026,373 A | 6/1991 | Ray et al. .................. 606/61 |
| 5,078,746 A | 1/1992 | Garner ....................... 623/16 |
| 5,092,891 A | 3/1992 | Kummer et al. ............. 623/16 |
| 5,112,354 A | 5/1992 | Sires .......................... 623/16 |
| 5,152,791 A | 10/1992 | Hakamatsuka et al. ....... 623/16 |
| 5,171,275 A | 12/1992 | Ling et al. .................. 623/16 |
| 5,383,932 A | 1/1995 | Wilson et al. .............. 623/16 |
| 5,403,317 A | 4/1995 | Bonutti ....................... 606/80 |
| 5,423,817 A | 6/1995 | Lin ............................. 606/61 |
| 5,458,638 A | 10/1995 | Kuslich et al. .............. 623/17 |
| 5,484,437 A | 1/1996 | Michelson ................... 606/61 |
| 5,489,307 A | 2/1996 | Kuslich et al. .............. 623/17 |
| 5,489,308 A | 2/1996 | Kuslich et al. .............. 623/17 |
| 5,501,706 A | 3/1996 | Arenberg .................... 623/16 |
| 5,571,192 A | 11/1996 | Schönhöffer ................. 623/17 |
| 5,591,235 A | 1/1997 | Kuslich ....................... 623/17 |

(List continued on next page.)

FOREIGN PATENT DOCUMENTS

| | | |
|---|---|---|
| DE | 44 23 257 A1 | 11/1996 |
| DE | 299 13 200 U1 | 10/1999 |
| EP | 0 505 634 A1 | 9/1992 |

(List continued on next page.)

OTHER PUBLICATIONS

Fred H. Albee, *Bone Graft Surgery in Disease, Injury and Deformity*, D. Appleton–Century Company, Inc., New York, 1940, pp. 30, 114, 151, 155, 164, 212, 256–257, 311–313.

Fred H. Albee, "Bone Surgery With Machine Tools," *Scientific American*, Apr., 1936, pp. 178–181.

Fred. H. Albee, *Bone–Graft Surgery*, W. B. Saunders Company, Philadelphia, Pennsylvania, 1915, pp. 145, 165–66, 171, 368–369.

*Primary Examiner*—Todd E. Manahan
(74) *Attorney, Agent, or Firm*—Pennie & Edmonds LLP

(57) ABSTRACT

The present invention relates to plugs for filling vacancies in bone tissue. The plugs include a body and at least one end cap that are coupled together and may be formed from bone. The body of the plug may be a sleeve, and the plug may further include an insert configured and dimensioned to be received in the sleeve.

55 Claims, 24 Drawing Sheets

U.S. PATENT DOCUMENTS

| | | | |
|---|---|---|---|
| 5,593,409 A | 1/1997 | Michelson | 606/61 |
| 5,607,474 A | 3/1997 | Athanasiou et al. | 623/11 |
| 5,645,598 A | 7/1997 | Brosnahan, III | 623/17 |
| 5,683,394 A | 11/1997 | Rinner | 606/86 |
| 5,702,449 A | 12/1997 | McKay | 623/17 |
| 5,702,453 A | 12/1997 | Rabbe et al. | 623/17 |
| 5,709,683 A | 1/1998 | Bagby | 606/61 |
| 5,722,977 A | 3/1998 | Wilhelmy | 606/84 |
| 5,728,159 A | 3/1998 | Stroever et al. | 623/16 |
| 5,741,253 A | 4/1998 | Michelson | 606/61 |
| 5,766,252 A | 6/1998 | Henry et al. | 623/17 |
| 5,766,253 A | 6/1998 | Brosnahan, III | 623/17 |
| 5,769,897 A | 6/1998 | Härle | 623/16 |
| 5,776,197 A | 7/1998 | Rabbe et al. | 623/17 |
| 5,776,198 A | 7/1998 | Rabbe et al. | 623/17 |
| 5,776,199 A | 7/1998 | Michelson | 623/17 |
| 5,782,917 A | 7/1998 | Carn | 623/16 |
| 5,785,710 A | 7/1998 | Michelson | 606/61 |
| 5,814,084 A | 9/1998 | Grivas et al. | 623/16 |
| 5,824,088 A | 10/1998 | Kirsch | 623/16 |
| 5,861,043 A | 1/1999 | Carn | 623/16 |
| 5,865,849 A | 2/1999 | Stone | 623/18 |
| 5,868,749 A | 2/1999 | Reed | 606/76 |
| 5,876,452 A | 3/1999 | Athanasiou et al. | 623/16 |
| 5,876,455 A | 3/1999 | Harwin | 623/16 |
| 5,879,403 A | 3/1999 | Ostiguy et al. | 623/22 |
| 5,885,299 A | 3/1999 | Winslow et al. | 606/99 |
| 5,888,219 A | 3/1999 | Bonutti | 623/11 |
| 5,895,426 A | 4/1999 | Scarborough et al. | 623/17 |
| 5,899,939 A | 5/1999 | Boyce et al. | 623/16 |
| 5,902,338 A | 5/1999 | Stone | 623/13 |
| 5,904,719 A | 5/1999 | Errico et al. | 623/17 |
| 5,910,315 A | 6/1999 | Stevenson et al. | 424/422 |
| 5,922,027 A | 7/1999 | Stone | 623/11 |
| 5,935,169 A | 8/1999 | Chan | 623/16 |
| 5,944,755 A | 8/1999 | Stone | 623/16 |
| 5,968,047 A | 10/1999 | Reed | 606/76 |
| 5,968,098 A | 10/1999 | Winslow | 623/17 |
| 5,972,034 A | 10/1999 | Hofmann et al. | 623/23 |
| 5,972,368 A | 10/1999 | McKay | 424/423 |
| 5,984,967 A | 11/1999 | Zdeblick et al. | 623/17 |
| 5,989,289 A | 11/1999 | Coates et al. | 623/17 |
| 5,997,580 A | 12/1999 | Mastrorio et al. | 623/22 |
| 5,997,581 A | 12/1999 | Khalili | 623/23 |
| 6,005,161 A | 12/1999 | Brekke et al. | 623/16 |
| 6,008,433 A | 12/1999 | Stone | 623/16 |
| 6,013,853 A | 1/2000 | Athanasiou et al. | 623/11 |
| 6,025,538 A | 2/2000 | Yaccarino, III | 623/16 |
| 6,033,405 A | 3/2000 | Winslow et al. | 606/61 |
| 6,033,438 A | 3/2000 | Bianchi et al. | 623/17 |
| 6,039,762 A | 3/2000 | McKay | 623/17 |
| 6,045,554 A | 4/2000 | Grooms et al. | 606/73 |
| 6,045,580 A | 4/2000 | Scarborough et al. | 623/17 |
| 6,053,916 A | 4/2000 | Moore | 606/61 |
| 6,059,790 A | 5/2000 | Sand et al. | 606/99 |
| 6,096,081 A | 8/2000 | Grivas et al. | 623/17.11 |
| 6,110,482 A | 8/2000 | Khouri et al. | 424/423 |
| 6,111,164 A | 8/2000 | Rainey et al. | 623/16 |
| 6,123,731 A | 9/2000 | Boyce et al. | 623/23.63 |
| 6,129,763 A | 10/2000 | Chauvin et al. | 623/17 |
| 6,143,030 A | 11/2000 | Schroder | 623/16.11 |
| 6,143,033 A | 11/2000 | Paul et al. | 623/17.11 |
| 6,146,420 A | 11/2000 | McKay | 623/17 |
| 6,187,329 B1 | 2/2001 | Agrawal et al. | 424/426 |
| 6,200,347 B1 | 3/2001 | Anderson et al. | 623/16.11 |
| 6,261,586 B1 | 7/2001 | McKay | 424/423 |
| 6,264,695 B1 | 7/2001 | Stoy | 623/17.16 |
| 6,270,528 B1 | 8/2001 | McKay | 623/17.11 |
| 6,371,988 B1 | 4/2002 | Pafford et al. | 623/17.11 |
| 6,398,811 B1 | 6/2002 | McKay | 623/17.16 |
| 6,458,158 B1 | 10/2002 | Anderson et al. | 623/16.11 |
| 6,494,883 B1 | 12/2002 | Ferree | 606/61 |
| 6,508,818 B2 | 1/2003 | Steiner et al. | 606/69 |
| 2001/0001129 A1 | 5/2001 | McKay et al. | 623/17.16 |
| 2001/0007072 A1 | 7/2001 | Steiner et al. | 606/57 |
| 2001/0010021 A1 | 7/2001 | Boyd et al. | 623/17.13 |
| 2002/0106393 A1 | 8/2002 | Bianchi et al. | 424/423 |

FOREIGN PATENT DOCUMENTS

| | | |
|---|---|---|
| FR | 2 753 368 | 3/1998 |
| SU | 1465040 | 3/1989 |
| WO | WO 94/26211 | 11/1994 |
| WO | WO 96/39988 | 12/1996 |
| WO | WO 97/25945 | 7/1997 |
| WO | WO 98/17209 | 4/1998 |
| WO | WO 98/38948 | 9/1998 |
| WO | WO 98/55052 | 12/1998 |
| WO | WO 98/56319 | 12/1998 |
| WO | WO 98/56433 | 12/1998 |
| WO | WO 99/09914 | 3/1999 |
| WO | WO 99/38461 | 8/1999 |
| WO | WO 99/56675 | 11/1999 |
| WO | WO 00/07527 | 2/2000 |
| WO | WO 00/07528 | 2/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/74607 | 12/2000 |

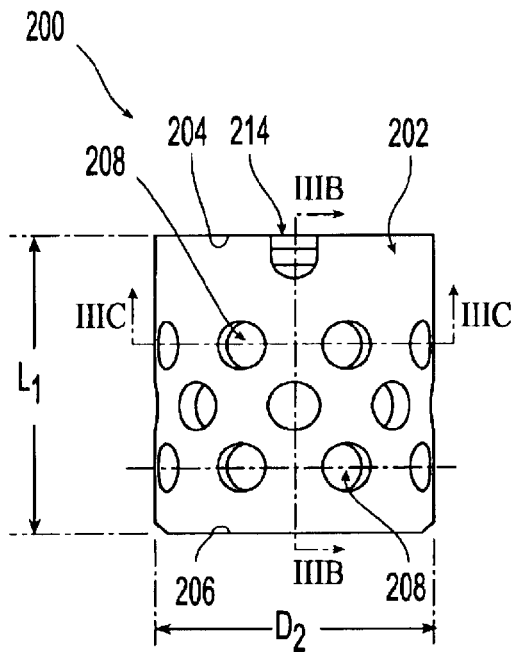
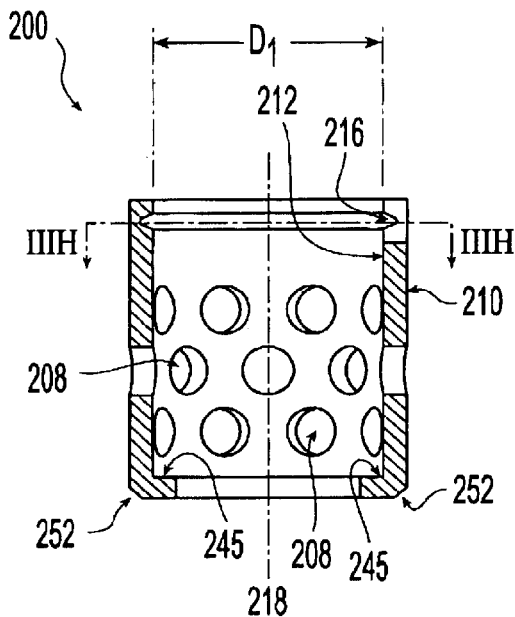
FIG. 3A  FIG. 3B
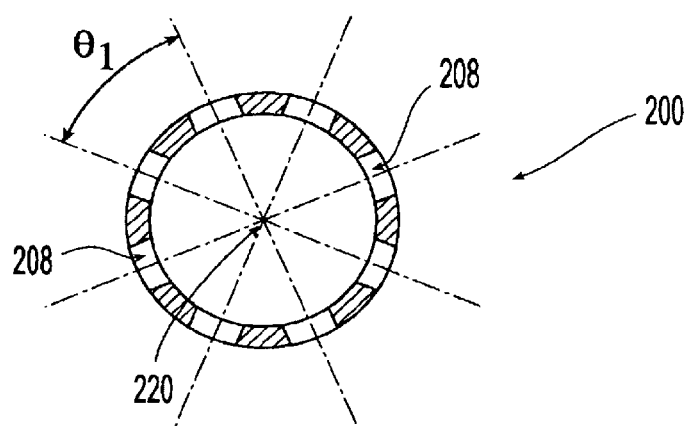
FIG. 3C

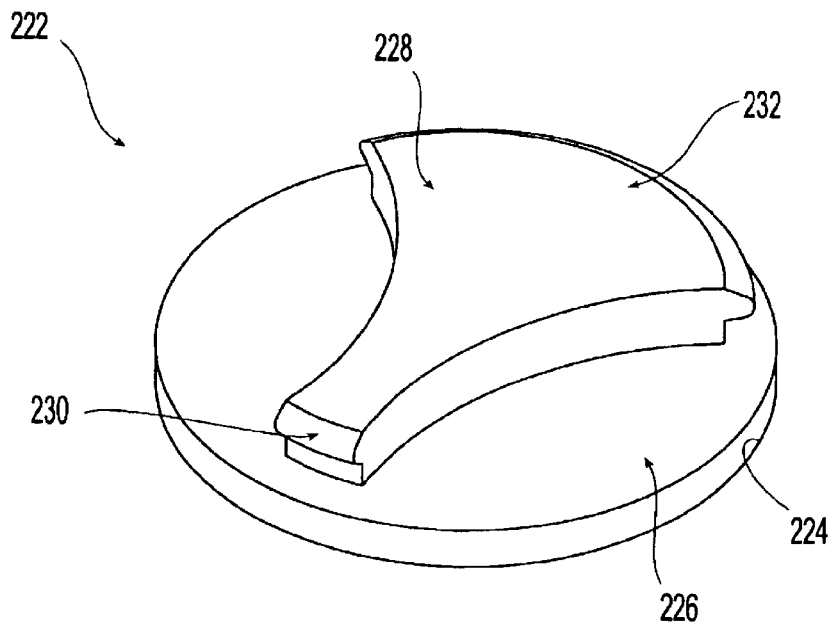
FIG. 3D
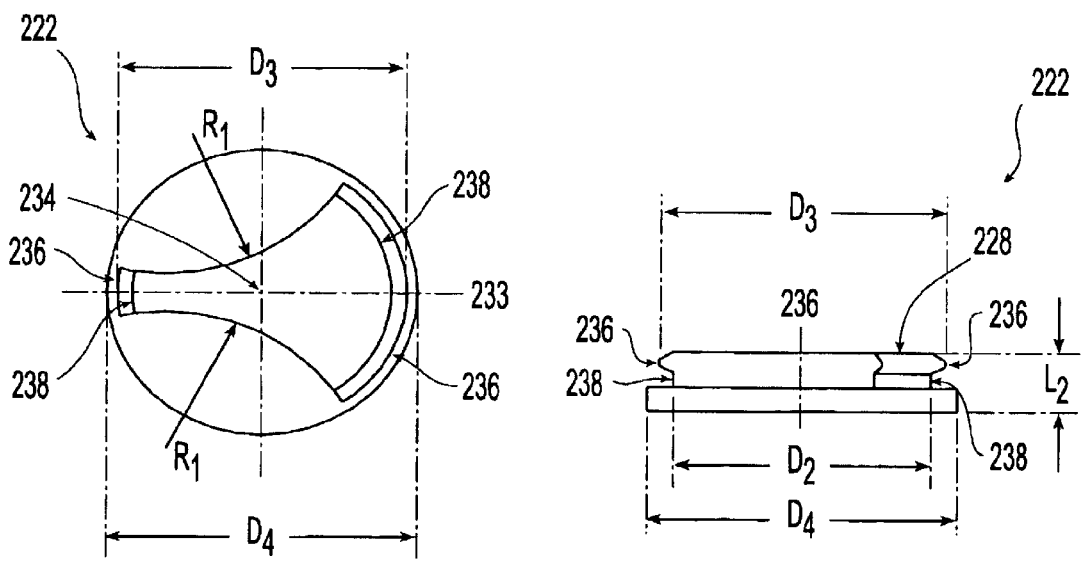
FIG. 3E   FIG. 3F

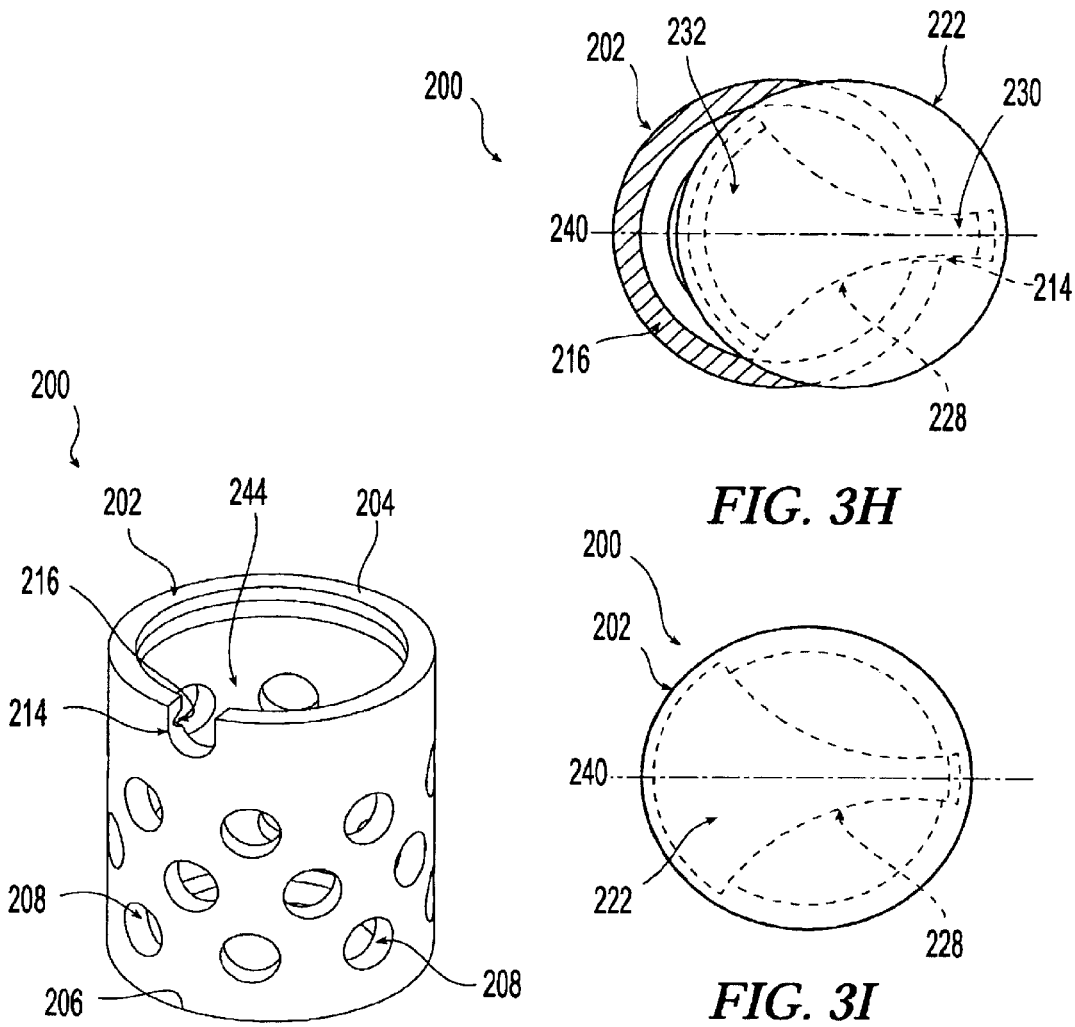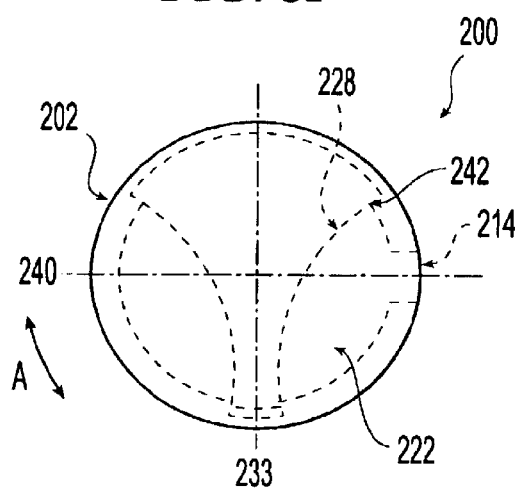

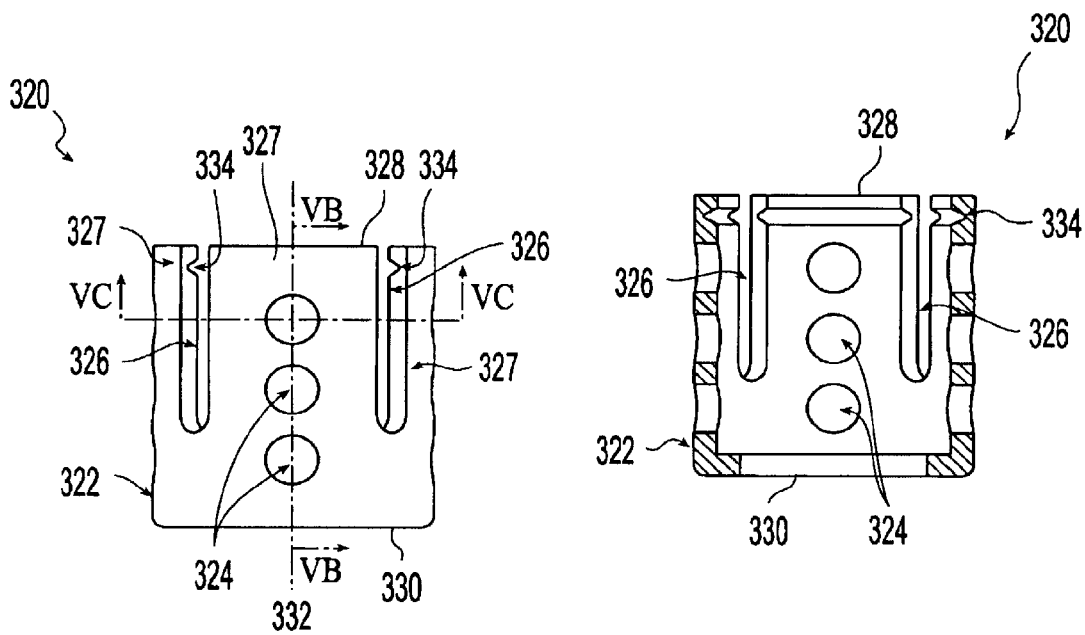
FIG. 5A
FIG. 5B
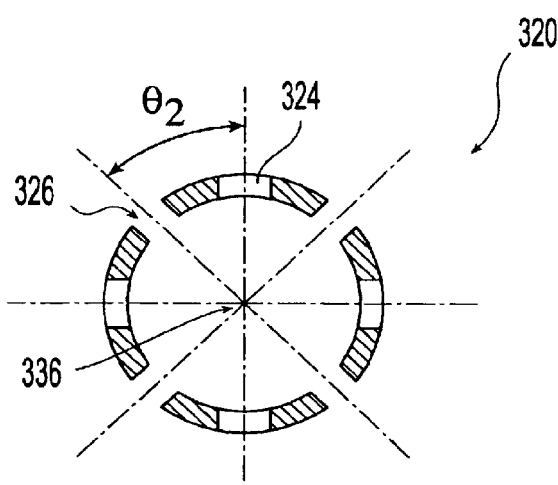
FIG. 5C

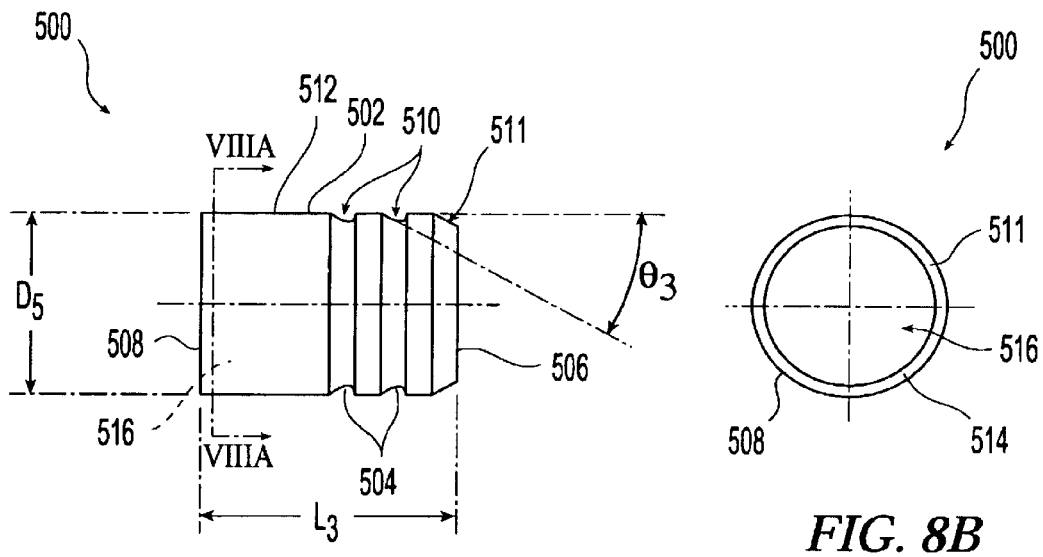
FIG. 8A
FIG. 8B
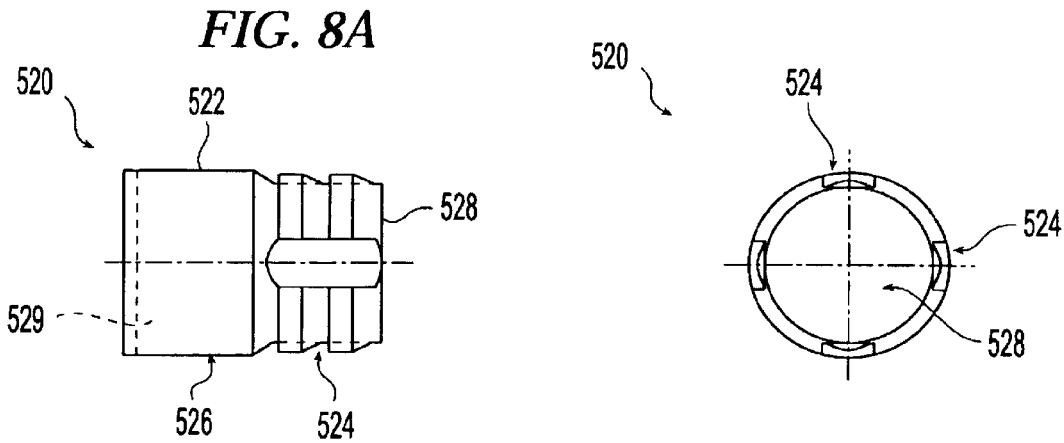
FIG. 9A
FIG. 9B
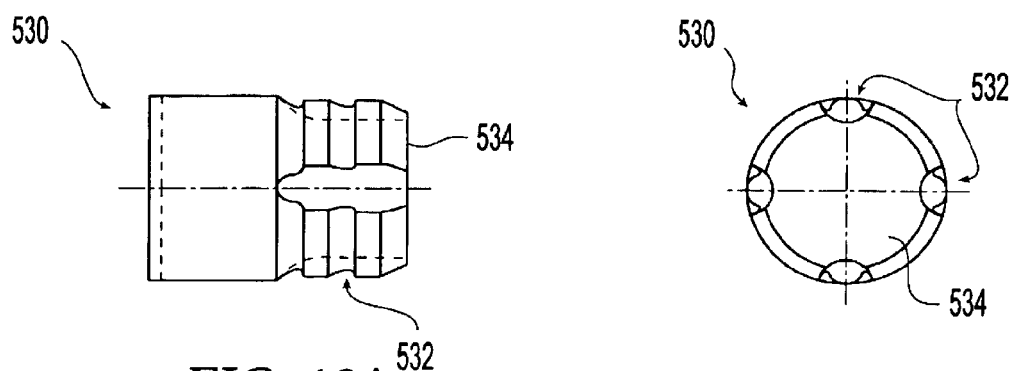
FIG. 10A
FIG. 10B

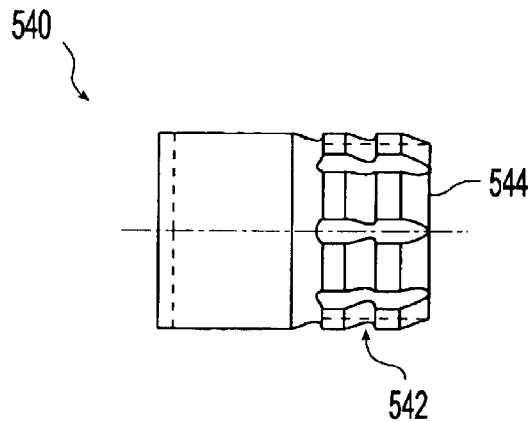
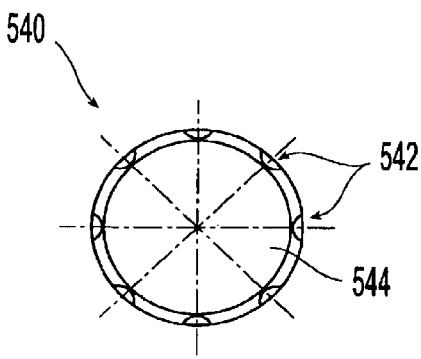
FIG. 11A  FIG. 11B
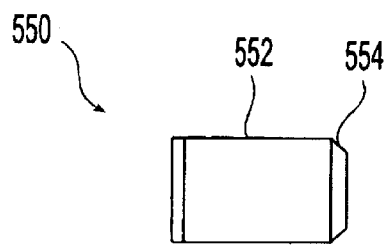
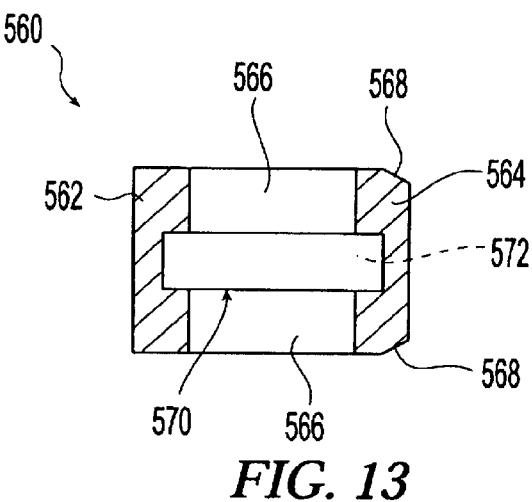
FIG. 12  FIG. 13
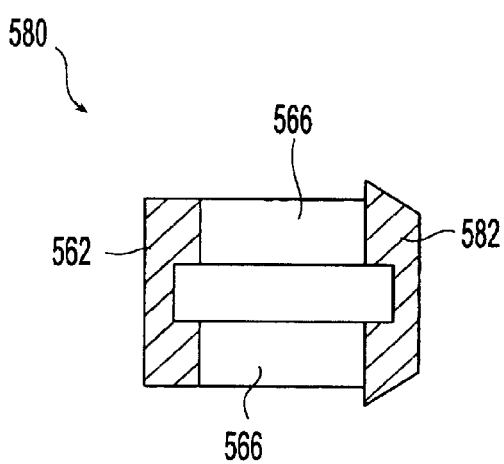
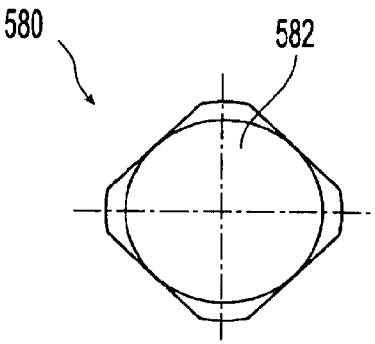
FIG. 14A  FIG. 14B

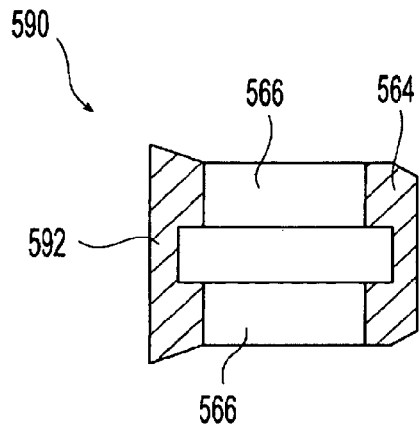
FIG. 15A
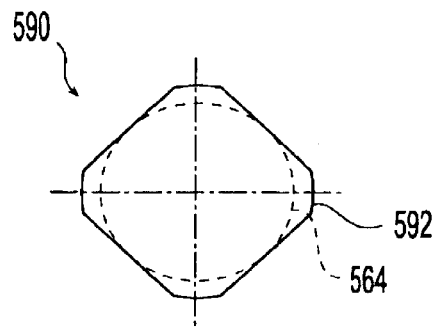
FIG. 15B
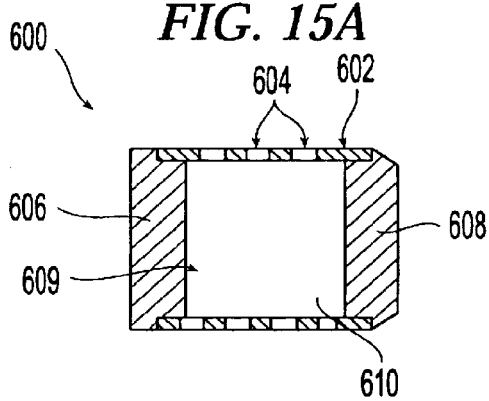
FIG. 16
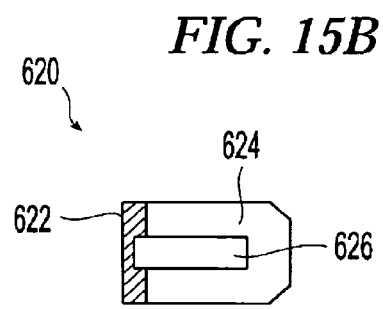
FIG. 17
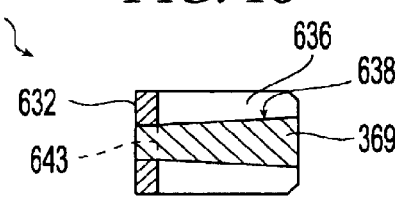
FIG. 18
FIG. 19
FIG. 20
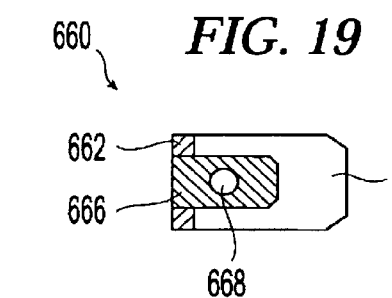
FIG. 21

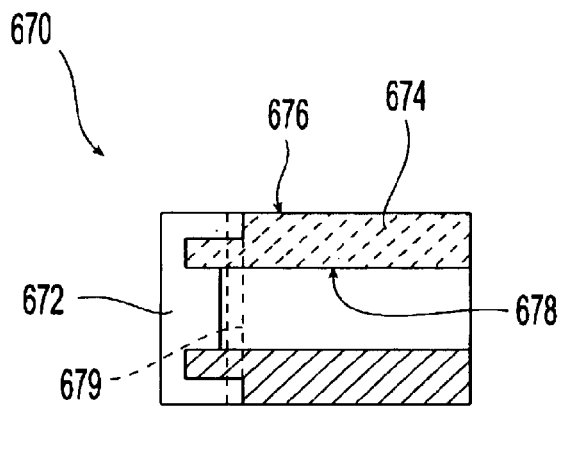
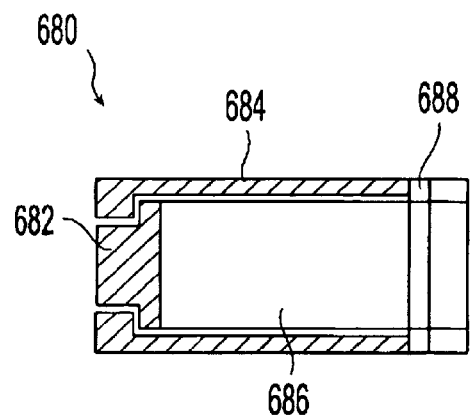
*FIG. 22*     *FIG. 23*
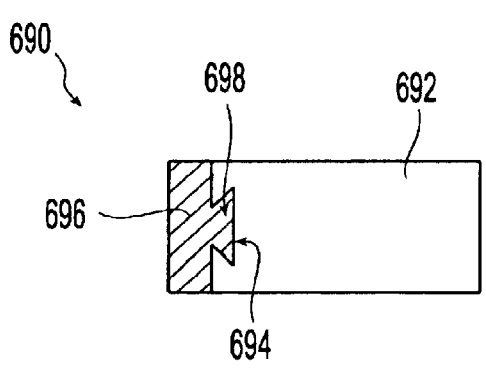
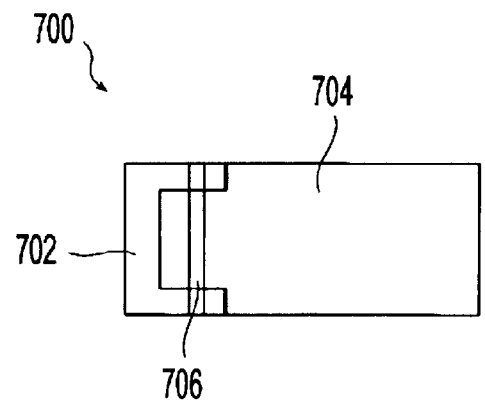
*FIG. 24*     *FIG. 25*
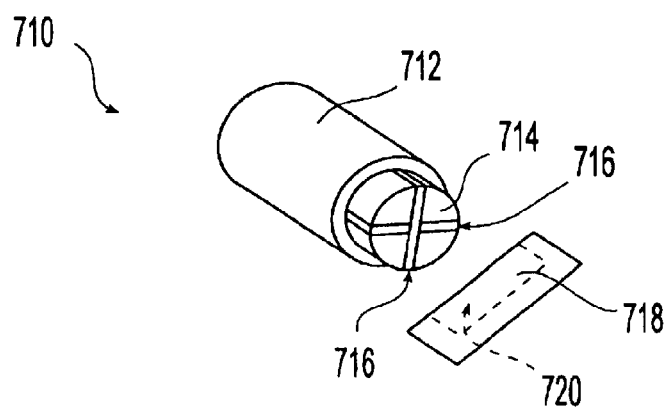
*FIG. 26*

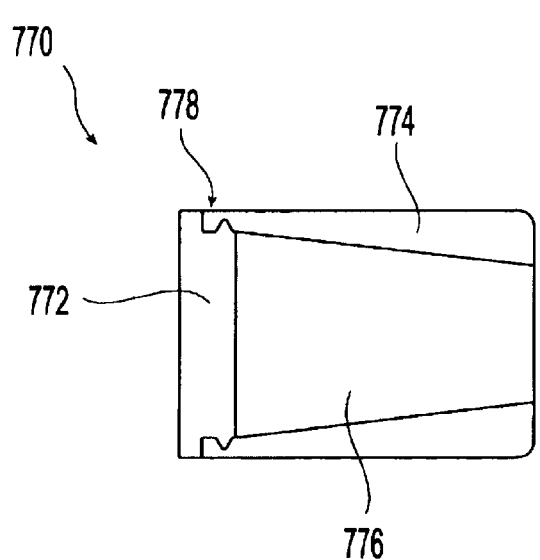
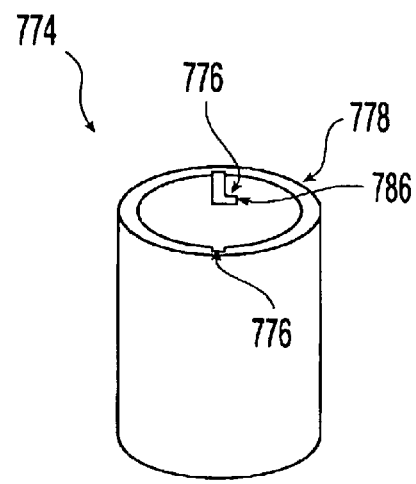
*FIG. 30A*  *FIG. 30B*
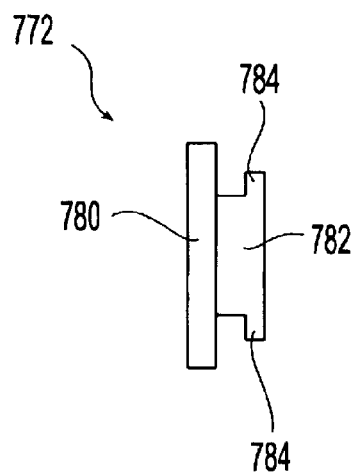
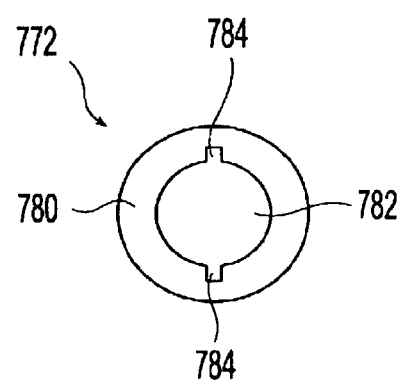
*FIG. 30C*  *FIG. 30D*

PLUGS FOR FILLING BONY DEFECTS

CROSS-REFERENCE TO RELATED APPLICATIONS

The benefit of Provisional Application No. 60/191,099 filed Mar. 22, 2000 is claimed under 35 U.S.C. §119(e).

FIELD OF THE INVENTION

The invention relates to an implant for orthopedic applications. More particularly, the invention is related to plugs for filling vacancies in bone tissue.

BACKGROUND OF THE INVENTION

Bone grafts have become an important and accepted means for treating bone fractures and defects. In the United States alone, approximately half a million bone grafting procedures are performed annually, directed to a diverse array of medical interventions for complications such as fractures involving bone loss, injuries or other conditions necessitating immobilization by fusion (such as for the spine or joints), and other bone defects that may be present due to trauma, infection, or disease. Bone grafting involves the surgical transplantation of pieces of bone within the body, and generally is effectuated through the use of graft material acquired from a human source. This is primarily due to the limited applicability of xenografts, transplants from another species.

Orthopedic autografts or autogenous grafts involve source bone acquired from the same individual that will receive the transplantation. Thus, this type of transplant moves bony material from one location in a body to another location in the same body, and has the advantage of producing minimal immunological complications. It is not always possible or even desirable to use an autograft. The acquisition of bone material from the body of a patient typically requires a separate operation from the implantation procedure. Furthermore, the removal of material, oftentimes involving the use of healthy material from the pelvic area or ribs, has the tendency to result in additional patient discomfort during rehabilitation, particularly at the location of the material removal. Grafts formed from synthetic material have also been developed, but the difficulty in mimicking the properties of bone limits the efficacy of these implants.

As a result of the challenges posed by autografts and synthetic grafts, many orthopedic procedures alternatively involve the use of allografts, which are bone grafts from other human sources (normally cadavers). The bone grafts, for example, are placed in a host bone and serve as the substructure for supporting new bone tissue growth from the host bone. The grafts are sculpted to assume a shape that is appropriate for insertion at the fracture or defect area, and often require fixation to that area as by screws or pins. Due to the availability of allograft source material, and the widespread acceptance of this material in the medical community, the use of allograft tissues is certain to expand in the field of musculoskeletal surgery.

Notably, the various bones of the body such as the femur (thigh), tibia and fibula (leg), humerus (upper arm), radius and ulna (lower arm) have geometries that vary considerably. In addition, the lengths of these bones vary; for example, in an adult the lengths may vary from 47 centimeters (femur) to 26 centimeters (radius). Furthermore, the shape of the cross section of each type of bone varies considerably, as does the shape of any given bone over its length. While a femur has a generally rounded outer shape, a tibia has a generally triangular outer shape. Also, the wall thickness varies in different areas of the cross-section of each bone. Thus, the use of any given bone to produce an implant component may be a function of the bone's dimensions and geometry. Machining of bones, however, may permit the production of implant components with standardized dimensions.

As a collagen-rich and mineralized tissue, bone is composed of about forty percent organic material (mainly collagen), with the remainder being inorganic material (mainly a near-hydroxyapatite composition resembling $3Ca_3(PO_4)_2 \cdot Ca(OH)_2$). Structurally, the collagen assumes a fibril formation, with hydroxyapatite crystals disposed along the length of the fibril, and the individual fibrils are disposed parallel to each other forming fibers. Depending on the type of bone, the fibrils are either interwoven, or arranged in lamellae that are disposed perpendicular to each other.

There is little doubt that bone tissues have a complex design, and there are substantial variations in the properties of bone tissues with respect to the type of bone (i.e., leg, arm, vertebra) as well as the overall structure of each type. For example, when tested in the longitudinal direction, leg and arm bones have a modulus of elasticity of about 17 to 19 GPa, while vertebra tissue has a modulus of elasticity of less than 1 GPa. The tensile strength of leg and arm bones varies between about 120 MPa and about 150 MPa, while vertebra have a tensile strength of less than 4 MPa. Notably, the compressive strength of bone varies, with the femur and humerus each having a maximum compressive strength of about 167 MPa and 132 MPa respectively. Again, the vertebra have a far lower compressive strength of no more than about 10 MPa.

With respect to the overall structure of a given bone, the mechanical properties vary throughout the bone. For example, a long bone (leg bone) such as the femur has both compact bone and spongy bone. Cortical bone, the compact and dense bone that surrounds the marrow cavity, is generally solid and thus carries the majority of the load in major bones. Cancellous bone, the spongy inner bone, is generally porous and ductile, and when compared to cortical bone is only about one-third to one-quarter as dense, one-tenth to one-twentieth as stiff, but five times as ductile. While cancellous bone has a tensile strength of about 10–20 MPa and a density of about 0.7, cortical bone has a tensile strength of about 100–200 MPa and a density of about 2. Additionally, the strain to failure of cancellous bone is about 5–7%, while cortical bone can only withstand 1–3% strain before failure. It should also be noted that these mechanical characteristics may degrade as a result of numerous factors such as any chemical treatment applied to the bone material, and the manner of storage after removal but prior to implantation (i.e. drying of the bone).

Notably, implants of cancellous bone incorporate more readily with the surrounding host bone, due to the superior osteoconductive nature of cancelous bone as compared to cortical bone. Furthermore, cancellous bone from different regions of the body is known to have a range of porosities. For example, cancellous bone in the iliac crest has a different porosity from cancellous bone in a femoral head. Thus, the design of an implant using cancellous bone may be tailored to specifically incorporate material of a desired porosity.

It is essential to recognize the distinctions in the types and properties of bones when considering the design of implants. Surgeons often work with bones using similar tools as would be found in carpentry, adapted for use in the operating room environment. This suggests that bones have some properties which are similar to some types of wood, for example ease in sawing and drilling. Notably, however, are many differences from wood such as the abrasive nature of hydroxyapatite and the poor response to local heating during machining of a bone. The combination of tensile and compressive strengths found in bone, resulting from the properties of the collagen and hydroxyapatite, is thus more aptly compared to the tensile and compressive strengths found in reinforced concrete, due to steel and cement. Furthermore, while wood is readily available in considerable quantity, bone material is an extremely limited resource that must be used in an extremely efficient manner.

Various types of bone grafts are known. For example, as disclosed in U.S. Pat. No. 5,989,289 to Coates et al., a spinal spacer includes a body formed of a bone composition such as cortical bone. The spacer has walls that define a chamber that is sized to receive an osteogenic composition to facilitate bone growth.

U.S. Pat. No. 5,899,939 to Boyce et al. discloses a bone-derived implant for load-supporting applications. The implant has one or more layers of fully mineralized or partially demineralized cortical bone and, optionally, one or more layers of some other material. The layers constituting the implant are assembled into a unitary structure, as by joining layers to each other in edge-to-edge fashion in a manner analogous to planking.

With a rapidly increasing demand in the medical profession for devices incorporating bone material, the tremendous need for the tissue material itself, particularly allograft tissue material, presents a considerable challenge to the industry that supplies the material. Due to the size and shape of the bones from which the material is harvested, and the dimensional limitations of any particular type of bone in terms of naturally occurring length and thickness (i.e. cortical or cancellous), there is a need for a means by which individual bone fragments can be combined to form larger, integral implants that are more suitable for use in areas of larger fractures or defects. For example, the size of cortical bone fragments needed to repair a fracture or defect site is often not available in a thick enough form. While multiple fragments may together meet the size and shape requirements, several prominent concerns have placed a practical limitation on the implementation of this concept. There is considerable uncertainty regarding the structural integrity provided by fragments positioned adjacent to one another without bonding or other means of securing the fragments to each other. Moreover, there is concern over the possibility that a fragment may slip out of position, resulting in migration of the fragment and possible further damage in or near the area of implantation.

In addition, due to the geometry of bones such as the femur and tibia, all portions of the bones are not readily usable as a result of size limitations. Thus, prior art implants, specifically allografts, are produced with an inefficient use of source bones.

There is a need for new, fundamental approaches to working with and processing tissues, in particular allograft material, especially with regard to machining, mating, and assembling bone fragments. Specifically, there is a need for an implant that allows more efficient use of source material. More specifically, there is a need for an implant that is an integrated implant comprising two or more bone fragments that are interlocked to form a mechanically effective, strong unit.

SUMMARY OF THE INVENTION

The present invention is related to a plug for filling a vacancy in bone tissue. The plug includes a body and at least one end cap coupled together. The body may be a sleeve with a top end, a bottom end, an inner surface and an outer surface. An insert configured and dimensioned to be received in the sleeve may also be provided. The insert may be formed of cancellous bone which may have a fluid concentrated therein. The insert may be subjected to mechanical pressure to concentrate the fluid, which may be applied by aspiration. The fluid also may be concentrated by soaking.

In some embodiments, the insert is secured to at least one of the sleeve and end cap with at least one fastener that is selected from a screw, key, pin, peg, rivet, cotter, nail, spike, bolt, stud, staple, boss, clamp, clip, dowel, stake, hook, anchor, tie, band, crimp, and wedge. At least one of the sleeve, end cap, insert, and fastener may be formed from partially demineralized or demineralized bone, and at least two of the sleeve, end cap, insert, and fastener may be bonded together with a bonding agent. At least one of the sleeve, end cap, insert, and fastener may be at least partially dehydrated to loosely fit within a surrounding mating surface. At least one of the sleeve, end cap, and insert may include alignment indicia. In some embodiments, the sleeve may be packed with at least one of bone chips, bone particulate, bone fibers, bone growth materials, hydroxyapatite, metal, resorbable material, polymer, ceramic, and bone cement.

In some embodiments, the sleeve also may include at least one through-hole extending from the inner surface to the outer surface, and the sleeve may be cylindrical. In addition, the sleeve may include at least one depression extending from the outer surface toward the inner surface. Furthermore, the sleeve may include a plurality of fingers formed integrally therewith.

The body and the at least one end cap of the plug may be formed from bone, with the sleeve and end cap being formed of cortical bone.

The present invention also is related to a plug for filling a vacant region in anatomical bone. The plug includes a body with a top end, a bottom end, and an outer surface disposed between the top and bottom ends. In addition, the plug includes at least one cap disposed at an end of the body, with the body and at least one cap being formed from bone. In some embodiments, the body and cap are integrally formed. The body and cap may be formed from a section of a long bone taken transverse to a long axis of the long bone, with the body including a through-hole formed by a canal in the long bone. In another embodiment, the body may be formed of cancellous bone and the cap may be formed of cortical bone.

The present invention further relates to a method for filling a vacancy in bone, including: inserting a filler into a portion of the vacancy, the filler comprising at least one of bone chips, bone particulate, bone fibers, bone-growth materials, hydroxyapatite, metal, resorbable material, polymer, ceramic, and bone cement; and fitting a cap to the vacancy to seal the filler therein.

BRIEF DESCRIPTION OF THE DRAWINGS

Preferred features of the present invention are disclosed in the accompanying drawings, wherein similar reference characters denote similar elements throughout the several views, and wherein:

FIG. 3A shows a side view of a sleeve for a plug according to the present invention;

FIG. 3B shows a cross-section of the sleeve of FIG. 3A through line IIIB—IIIB;

FIG. 3C shows a cross-section of the sleeve of FIG. 3A through line IIIC—IIIC;

FIG. 3D shows a perspective view of a cap according to the present invention;

FIG. 3E shows a bottom view of the cap of FIG. 3D;

FIG. 3F shows a side view of the cap of FIG. 3D;

FIG. 3G shows a perspective view of the sleeve of FIG. 3A;

FIGS. 3H to 3J show the installation of the cap of FIG. 3D on the sleeve of FIG. 3G;

FIG. 5A shows a side view of an additional embodiment of a sleeve for a plug with fingers according to the present invention;

FIG. 5B shows a cross-section of the sleeve of FIG. 5A through line VB—VB;

FIG. 5C shows a cross-section of the sleeve of FIG. 5A through line VC—VC;

FIG. 8A shows a side view of another plug according to the present invention;

FIG. 8B shows a side view of the plug of FIG. 8A;

FIG. 9A shows a side view of another plug according to the present invention;

FIG. 9B shows a side view of the plug of FIG. 9A;

FIG. 10A shows a side view of another plug according to the present invention;

FIG. 10B shows a side view of the plug of FIG. 10A;

FIG. 11A shows a side view of another plug according to the present invention;

FIG. 11B shows a side view of the plug of FIG. 11A;

FIG. 12 shows a side view of yet another plug according to the present invention;

FIG. 13 shows a side view in cross-section of another plug according to the present invention;

FIG. 14A shows a side view in cross-section of another plug according to the present invention;

FIG. 14B shows a side view of the plug of FIG. 14A;

FIG. 15A shows a side view in cross-section of another plug according to the present invention;

FIG. 15B shows a side view of the plug of FIG. 15A;

FIGS. 16 to 25 show side views in cross-section of additional embodiments of plugs according to the present invention;

FIGS. 26 and 27 show exploded perspective views of additional plugs according to the present invention;

FIG. 30A shows a side view in cross-section of another plug according to the present invention;

FIG. 30B shows a perspective view of the sleeve of FIG. 30A;

FIGS. 30C and 30D show a side view and bottom view, respectively, of the end cap of FIG. 30A;

DETAILED DESCRIPTION OF THE PREFERRED EMBODIMENTS

Figure 1A:
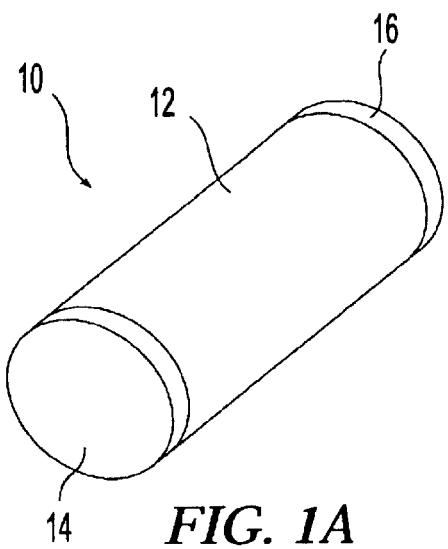
FIGS. 1A and 1B show perspective views of embodiments of plugs according to the present invention.
Figure 1B:
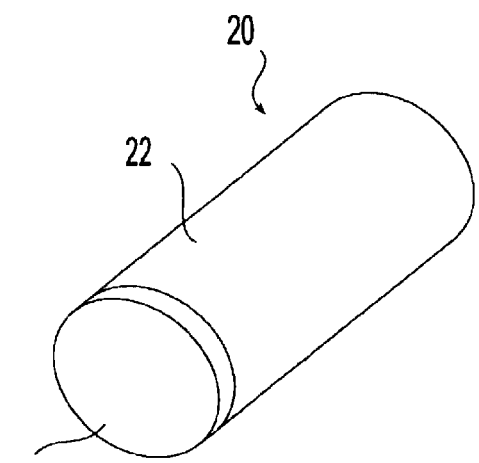
Figure 1C:
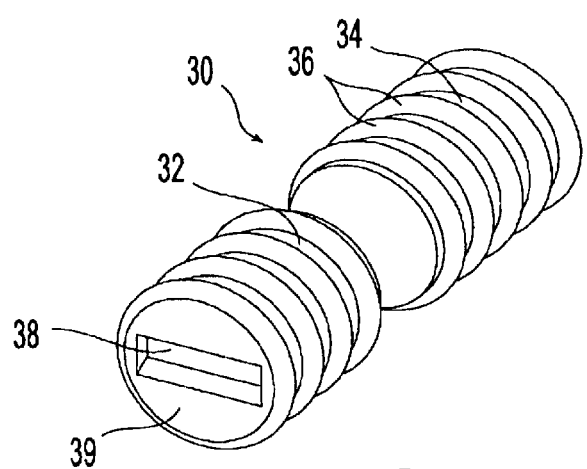
FIGS. 1C to 1G show exploded, perspective views of additional embodiments of plugs according to the present invention.
Figure 1D:
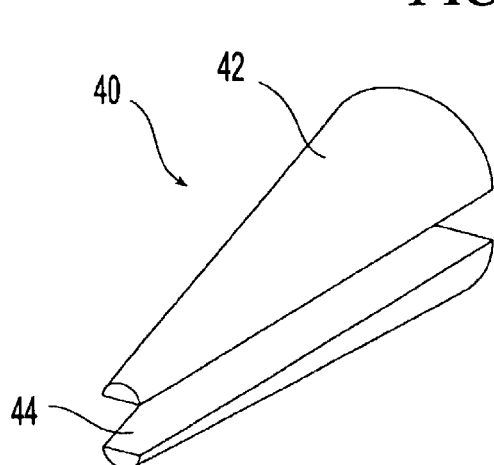
Figure 1E:
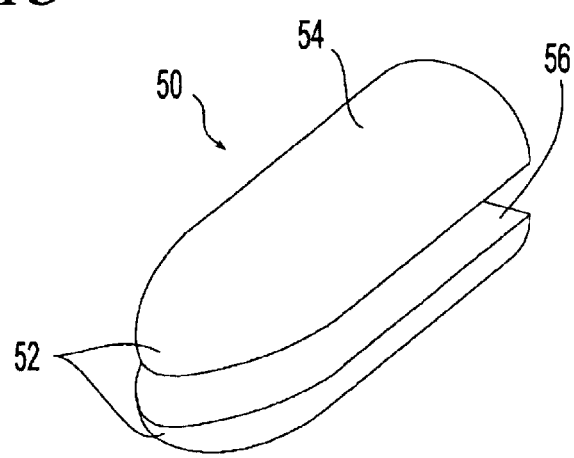

Any of a wide variety of different implant structures, particularly allograft, autograft, and/or xenograft implant structures, can be prepared according to the teachings of the present invention. While a representative selection of implant structures are described and depicted herein, additional disclosure is found in U.S. Provisional Application No. 60/191,099 filed Mar. 22, 2000, which is hereby incorporated herein in its entirety by reference, including all figures.

As used in the description of the present invention, the words fitting, interfitting, mating, locking, interlocking, meshing, and interlacing are all used generically to describe the joining of bone sections or pieces together. Thus, these words are not limited to the use of any particular manner of joining. Thus, for example, the press-fitting of one bone section within a cavity formed in another bone section may be described using any of the above-mentioned terms. In addition, although various preferred mechanical fastening approaches are described, the present invention allows the use of any mechanical device for joining two or more separate parts of an article or structure. Such mechanical devices include, but are not limited to the following: screws, keys, pins, pegs, rivets, cotters, nails, spikes, bolts, studs, staples, bosses, clamps, clips, dowels, stakes, hooks, anchors, ties, bands, and crimps. Also, bonding agents or other chemical means for joining two separate parts may be employed alone or in combination with the mechanical devices. Thus, as appropriate, the means disclosed herein for fixing bone sections to each other may be substituted, as with the above-mentioned mechanical devices, bonding devices, or chemical means. Furthermore, although particular types of joints are disclosed, the present invention is directed to the creation of implants that may be joined using other joints.

While the present invention is preferably directed to the creation of implants from allograft material, the present invention may also be applied to implants that utilize other materials, including but not limited to the following: xenograft, autograft, metals, alloys, ceramics, polymers, composites, and encapsulated fluids or gels. Furthermore, the implants described herein may be formed of materials with varying levels of porosity, such as by combined bone sections from different bones or different types of tissue having varying levels of porosity.

Also, the implants described herein may be formed of bone materials with varying mineral content. For example, cancellous or cortical bone may be provided in natural, partially demineralized, or demineralized states. Demineralization is typically achieved with a variety of chemical processing techniques, including the use of an acid such as hydrochloric acid, chelating agents, electrolysis or other treatments. The demineralization treatment removes the minerals contained in the natural bone, leaving collagen fibers with bone growth factors including bone morphogenic protein (BMP). Variation in the mechanical properties of bone sections is obtainable through demineralization. Advantageously, use of a demineralizing agent on natural bone transforms the properties of the bone from a stiff structure to a relatively pliable structure when hydrated. Some portions of interfitting bone components may be demineralized or partially demineralized in order to achieve improved interfitting. For example, a tissue form may include two bone components having portions that are coupled together with an interference fit. The interference fit may be enhanced if the surface region of one or more of the components is demineralized or partially demineralized so that it is pliable and exhibits some elasticity and/or malleability when hydrated.

In addition, while many of the embodiments described herein show bone components disposed at right angles, or joints formed with right angles, angles that are greater or less than ninety degrees may alternatively be used in implants of the present development.

The components that are used to create implants of the present invention may all be formed from cortical bone, all from cancellous bone, or a combination of components formed from cortical and cancellous bone. The interfitting of the components may be achieved through a variety of means, including but not limited to the following: pinning, bonding with a suitable bone bonding agent or chemical means, press fitting, threadably engaging (as by helically screwing one component into another), inserting a tapered component into a component with a matching inner surface, twist-locking, or other interlocking means such as will be described in other embodiments. While the present development preferably allows the creation of implants from all bone material, it is also anticipated that one or more components used to create the implants may be formed of non-bone material such as a synthetic or other material. Thus, while the implants disclosed herein are typically described as being formed primarily from bone, the implants alternatively may be formed in whole or in part from other materials such as hydroxyapatite, metal, resorbable material, polymer, and ceramic, and may additionally incorporate bone chips, bone particulate, bone fibers, bone growth materials, and bone cement. Also, while solid, cylindrical sleeve-like structures are described herein, the sleeves optionally may include perforations extending from outer to inner surfaces, or recesses formed in outer surfaces that do not extend through inner surfaces. Geometries such as circular depressions, dimples formed from a spherical geometry, diamond shapes, or rectangular shapes may be used.

Bones suitable for forming implants of the present invention include a radius, humerus, tibia, femur, fibula, or ulna, although other bones may be used.

The moisture content of the bone sections also may be varied to advantageously permit improved interlocking. Bone components initially may be provided with moisture content as follows: (1) bone in the natural state fresh out of the donor without freezing, (2) bone in the frozen state, typically at −40° C., with moisture content intact, (3) bone with moisture removed such as freeze-dried bone, and (4) bone in the hydrated state, such as when submersed in water. Using the expansion and contraction properties that can be obtained during heating and cooling of the bone material, and the concomitant resorption of moisture along with swelling for some bone material, permits an alternate approach to achieving a tight press-fit.

Turning to FIGS. 1A to 1J, tissue forms are shown in the shape of plugs suitable for implantation. Plugs may be created using a core drill or trephine system, or may be machined or otherwise formed from bone. For example, using a trephine system, essentially a dowel cutter for use with tissues, a cylindrical shaped plug may be cut in vivo from a tissue, such as a vertebral body or tissue from another location such as the hip. This material may be used as an autograft, which may serve as a plug to fill an anatomical defect or instead may serve as a strut to be inserted into another implant formed of bone to provide additional strength. A similarly sized plug of allograft material may be used to fill the hole created by the removal of autograft material. The plugs contemplated by the present invention, however, may be made of allograft or xenograft bone material as well, or combinations of autograft, allograft, and xenograft bone material. The plugs may also be formed from cancellous bone, cortical bone, or combinations thereof and the choice of such materials may be based on the materials properties obtainable from a given type of bone. For example, cancellous bone is available in a range of porosities based on the location in the body from which the bone is harvested. Extremely porous cancellous bone may be harvested from various areas such as the iliac crest, while less porous bone may be harvested from areas such as a tibial condyle. Thus, the materials properties—particularly the porosity—of the plugs may be selected to meet the needs of a given application. In addition, the plugs of the present invention may be formed either partially or completely using non-bone materials such as metals, alloys, ceramics, polymers, composites, and encapsulated fluids or gels.

Turning to the various embodiments of plugs according to the present invention, it should be noted that the plugs discloses herein may be of unitary construction, or may be formed from multiple pieces that are interfitted together. Thus, while the figures may show cross-sections of plugs or plugs formed with multiple pieces to produce a particular structure, it should be noted that the structures instead may be one-piece. In addition, although the plugs are generally described herein as being formed from bone or at least in part from bone, the plugs may additionally be formed completely from non-bone materials such as metals or ceramics. Also, while dimensions are indicated herein for plugs, it should be noted that much smaller plugs as well as much larger plugs also are contemplated following the general structures disclosed herein.

As shown in FIG. 1A, a cylindrical plug 10 according to the present invention includes a central region 12 and end caps 14, 16. Preferably, central region 12 is formed of cancellous bone material, while caps 14, 16 are formed of cortical bone material. Cortical bone material is placed at the ends of plug 10 due to its superior mechanical strength and lower porosity as compared to cancellous bone material. In alternate embodiments, central region 12 and end caps 14, 16 may be formed from other types of bone and or non-bone materials to suit a particular need.

Other embodiments of plugs according to the present invention are shown in FIGS. 1B to 1J. Plug 20 includes a body 22 and single end cap 24. Plug 30 is formed of two sections of bone 32, 34 that are interfitted together. Ribbing 36 may be provided along the length of plug 20, and a keyhole 38 may be provided at a head 39. Keyhole 38 preferably is sized to receive a screwdriver, or other suitable device, to facilitate the installation of plug 30 in an anatomical region. Alternate forms of keyhole 38 include recesses shaped in the form of a cruciform, hex, star, recess, or clover. In another embodiment, a tapered, conical shaped plug 40 may be formed from bone material. Plug 40 may be formed from a single piece of bone, or it may be formed of two or more pieces of bone that are interfitted together as shown for example with sections 42, 44. Similarly, a bullet shaped plug 50 with a blunt tip 52 may be formed from bone sections 54, 56.

Figure 1F:
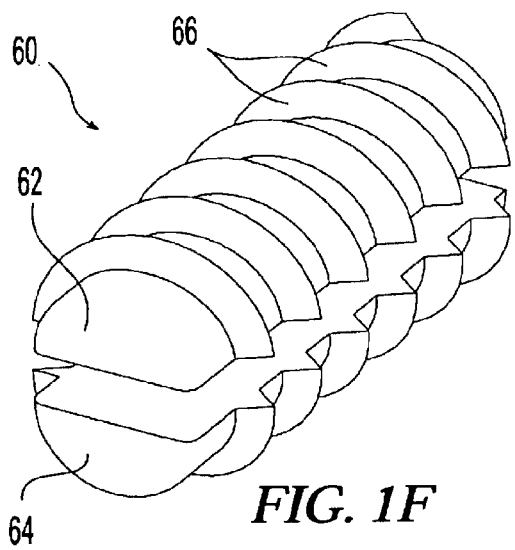
Figure 1G:
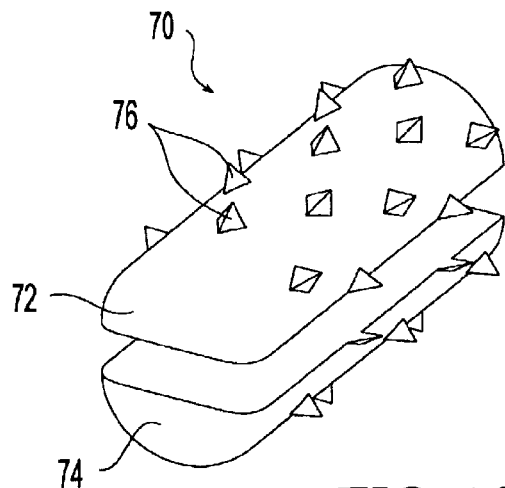

A plug 60 as shown in FIG. 1F is formed of bone sections 62, 64 that are interfitted together, and further includes threading 66 that is machined on the plug. A plug 70, also formed for example from two bone sections 72, 74 includes migration-resistance protrusions such as spurs or teeth 76 disposed around the circumference of the plug. Alternatively, a plug 70 could be formed from a single piece of bone or other material such as metal or ceramic.

Figure 1H:
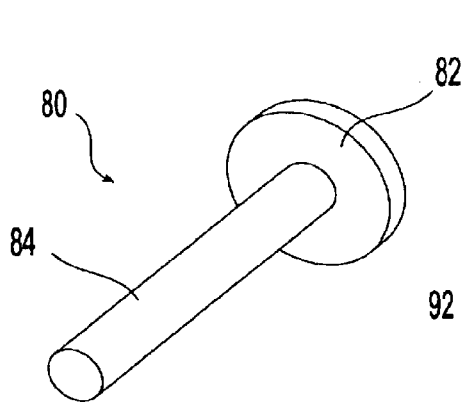
FIG. 1H shows a perspective view of another embodiment of a plug according to the present invention.
Figure 1I:
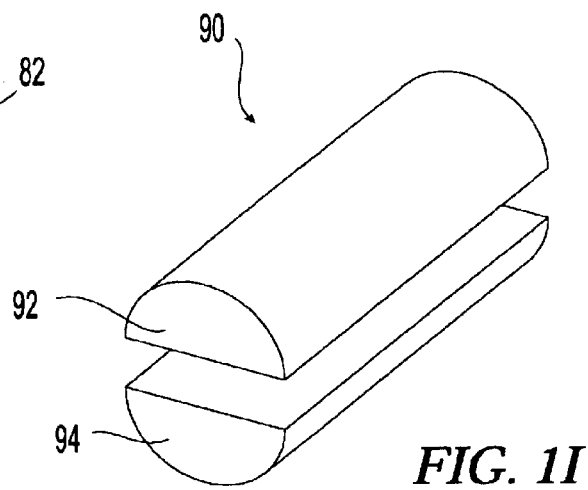
FIGS. 1I to 1J show exploded, perspective views of additional embodiments of plugs according to the present invention.
Figure 1J:
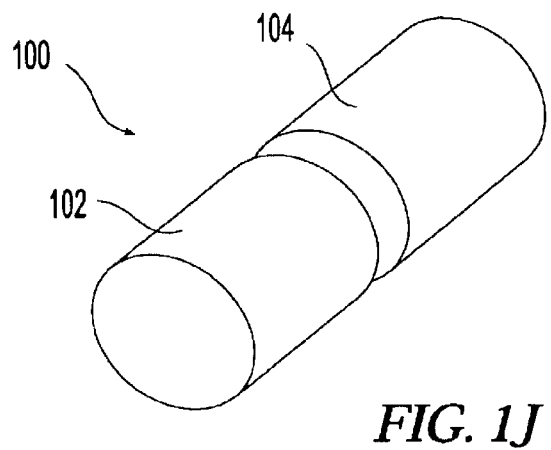

A plug 80 with an oversized head 82 and a shaft 84 is shown in FIG. 1H. As previously discussed with respect to embodiments with end caps, head 82 may be formed of cortical bone while shaft 84 may be formed of cancellous bone. Although plug 80 may be machined from one piece of bone, head 82 and shaft 84 may be separate bone pieces that are interfitted together. Similarly, plug 80 may incorporate non-bone material. Other designs of plugs include a plug 90 formed from two bone sections 92, 94 that are interfitted together along a longitudinal axis extending through the free ends of the sections, and plug 100 formed from bone sections 102, 104 that are interfitted together at one free end of each section. Alternate embodiments contemplated by the present invention include plugs formed of non-symmetrical bone sections, plugs formed from one piece of bone, and plugs formed from more than two pieces of bone with the sections joined together using joints, fasteners, or other techniques described above. In addition, the plugs may be formed using metal, resorbable material, plastic, or ceramic, as well as the various types of bone with various degrees of porosity as previously described. Plug may include sections of cortical bone, cancellous bone, metals ceramics, or other materials.

In some circumstances it is desirable not to fill an entire defect or vacant region in a bone with a single plug. For example, other material such as bone chips, slurries of bone particulate, bone fibers, bone-growth inducing substances, bone cement, or polymers may be inserted into the defect or vacancy, and sealed therein using a cap. Various forms of caps suitable for this purpose are shown in FIGS. 2A–2H. The caps may be created using allograft tissue. In alternate embodiments, the caps may be formed using metal, resorbable material, plastic, ceramic, autograft, or xenograft. The cap 110 shown in FIG. 2A includes a rounded head 112 and a body 114 which may be press-fit into a vacancy in bone, while cap 120 includes a flat head 122 and a body 124. Cap 130, shown in FIG. 2C, includes a cap 132, body 134, and migration-resistant protrusions 136, while cap 140 includes a head 142, body 144, and flange area 146 that functions similar to circumferentially distributed teeth. Another cap of the present invention, cap 150, includes a head 152 and a tapered body 154. A through-hole 156 may also be provided, for example, to permit a needle to gain access to the vacancy sealed by the cap. Such a hole may permit delivery of substances after the cap has been installed, or permit expansion of the cap as by inserting a component therein.

Figure 2A:
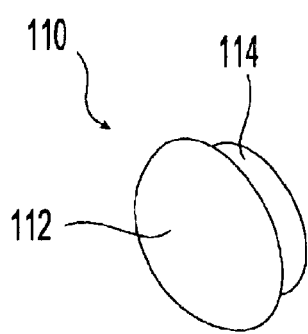
FIGS. 2A to 2H show perspective views of embodiments of caps according to the present invention.
Figure 2B:
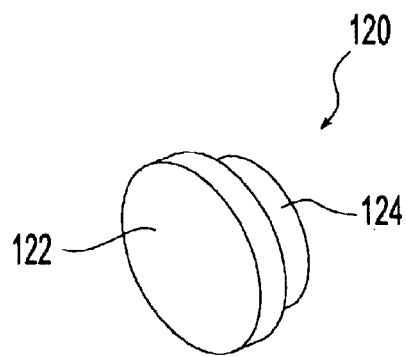
Figure 2C:
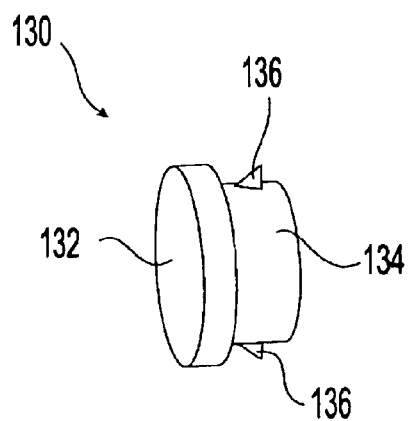
Figure 2D:
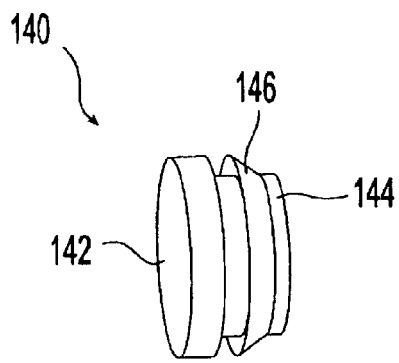
Figure 2E:
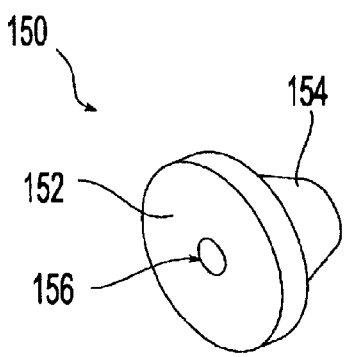
Figure 2F:
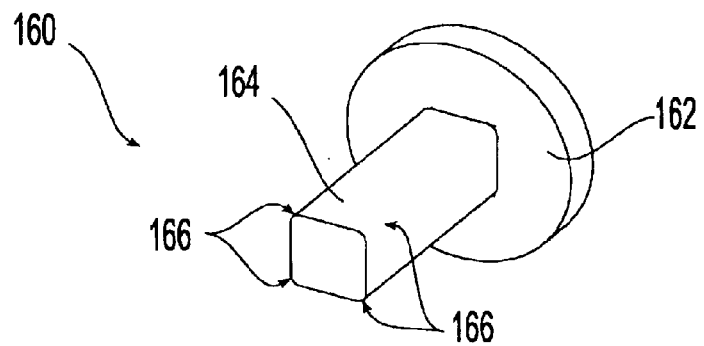

Cap 160, shown in FIG. 2F, includes a flat, circular head 162 and a generally rectangular body 164. Notably, the faces of body 164 meet to create four longitudinal radiused portions 166. When cap 160 is inserted in a suitably sized vacancy, the four radiused portions 166 provide four regions of contact with the walls of the vacancy. Such a construction facilitates press-fitting in the vacancy; a press-fit of a cap body that is closely shaped to conform to the walls of a defect may be difficult to achieve due to the tightness inherent in the fit itself. A less tight fit, as provided for example by body 164, may permit a press-fit to be achieved with less difficulty. While a press-fit with four radiused portions 166 of contact has been described, it is also contemplated that press-fits with other amounts of contact may be used.

Figure 2G:
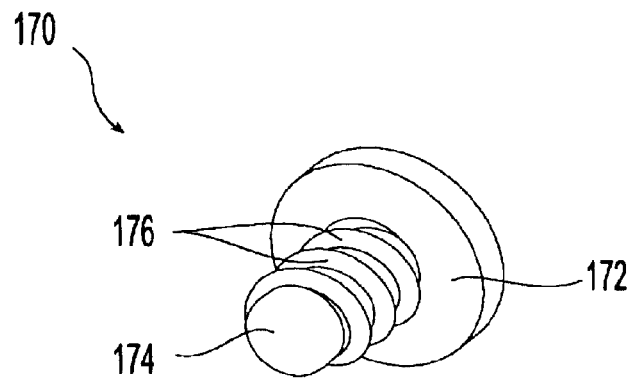
Figure 2H:
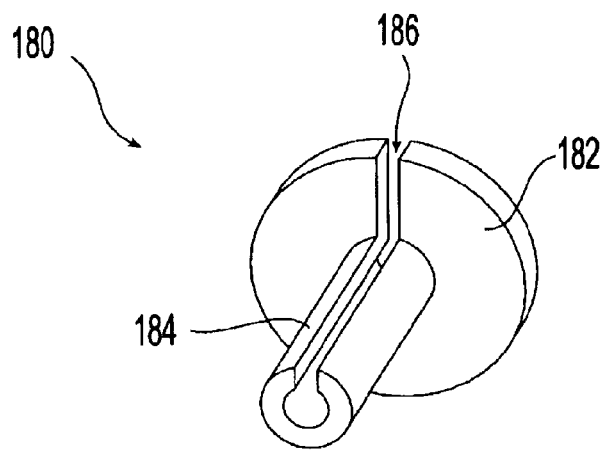

Several additional embodiments of caps are shown in FIGS. 2G and 2H. Cap 170 includes a head 172 and a body 174 with threading 176. Cap 180 includes a head 182 and a body 184. A slit 186 extends about halfway through head 182 and body 184. Slit 186 allows cap 180 to be compressed when inserted in a vacancy; after insertion, the cap may re-expand to more closely fit against the walls of the vacancy. Also, cap 180 may be inserted into a vacancy and expanded using a wedge or pin that is subsequently inserted into slit 186.

Figure 3K:
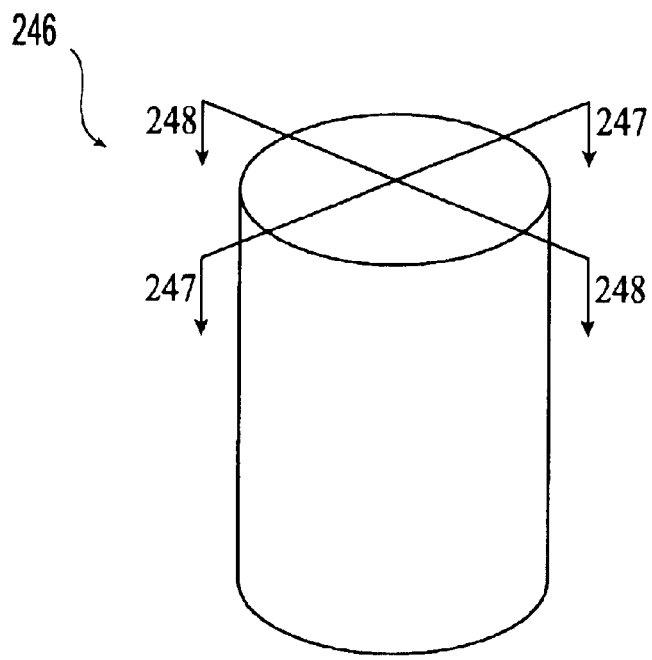
FIGS. 3K and 3L show perspective views of fillers according to the present invention.
Figure 3L:
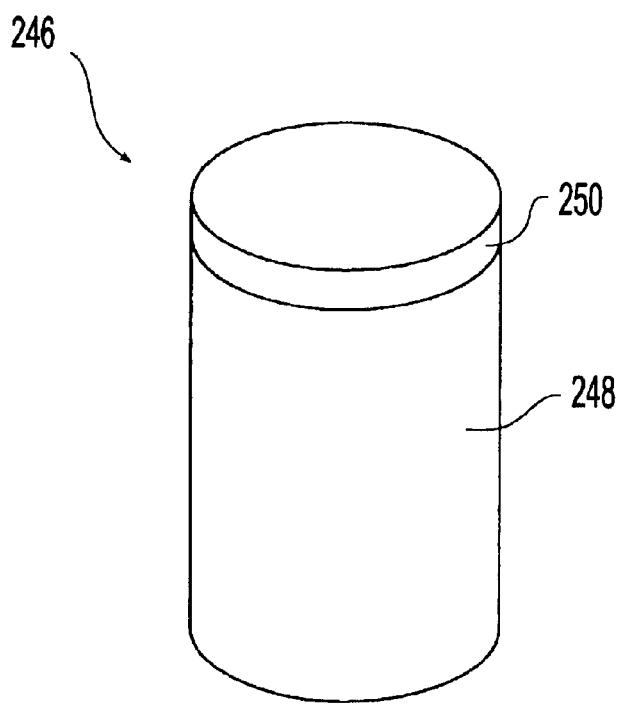
Figure 3M:
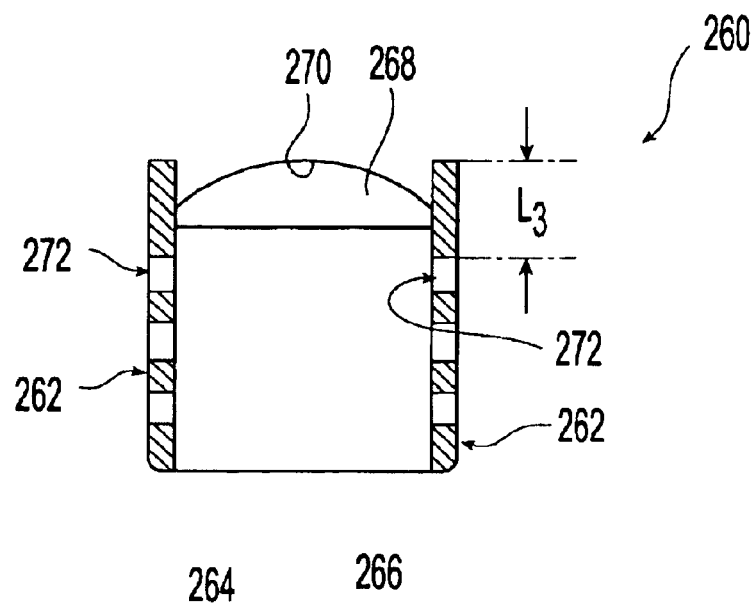
FIG. 3M shows a side view of a plug according to the present invention with a filler formed from a femoral head.

Referring initially to FIGS. 3A to 3C, a preferred embodiment of a plug according to the present invention is shown. Plug 200 includes a sleeve 202 with open, free ends 204, 206. Holes 208 extend from outer wall 210 to inner wall 212. Preferably, holes 208 are arranged in rows centered about parallel planes with respect to each other, around the circumference of plug 200. A slot 214 is disposed at a free end 204 and a circumferential groove 216 is cut into inner surface 212 proximate free end 204. A central axis 218 is disposed longitudinally about the center of plug 200, and preferably inner and outer diameters $D_1$, $D_2$, respectively, of plug 200 are generally constant, but may be tapered. In the preferred embodiment, holes 208 are offset by a generally constant angle $\theta_1$ with respect to each other, as measured from center 220 defined along axis 218. Preferably, angle $\theta_1$ is between about 35° and about 55° and more preferably about 45°. In a preferred embodiment, plug 200 has an inner diameter $D_1$ of between about 1.2 cm and 1.4 cm, an outer diameter $D_2$ of between about 1.5 cm and 1.7 cm, and a length $L_1$ of between about 1.6 cm and 2.0 cm. More preferably, inner diameter $D_1$, outer diameter $D_2$, and length $L_1$ are about 1.3 cm, 1.6 cm, and 1.9 cm, respectively. Holes 208 are preferably circular and have a diameter of between about 0.2 cm and about 0.5 cm, and more preferably about 0.35 cm. In alternate embodiments, holes 208 may be in other shapes such as elliptical or oblong geometries; the number of holes 208 as well as the alignment of holes 208 with respect to each other may be varied.

As shown in FIGS. 3D to 3F, a cap 222 suitable for coupling to sleeve 202 includes a top surface 224 and a bottom surface 226. A locking portion 228 preferably is integrally formed on bottom surface 226, and includes narrow and wide portions 230, 232, respectively, which are symmetrical about central line 233. The outer edges of narrow and wide portions 230, 232 are preferably disposed along the circumference of a circle centered about point 234 along central axis 236 of cap 222, with the diameter of the circle being smaller than that of outer diameter $D_2$ of sleeve 202. In particular, as shown in FIG. 3F, locking portion 228 of cap 222 includes a lip 236 and a wall 238. Preferably, outer diameter $D_4$ of cap 222 is about the same as outer diameter $D_2$ of sleeve 202, lip 236 of cap 222 has an outer diameter $D_3$ sized to fit and turn within groove 216 in sleeve 202, while wall 238 has an outer diameter $D_2$ sized to fit and turn proximate inner surface 212 of sleeve 202. In addition, locking portion 228 preferably tapers from wide portion 232 to narrow portion 230 along a radius of curvature $R_1$ of between about 0.5 cm and 1.1 cm, and more preferably 0.8 cm. Preferably, the overall thickness $L_2$ of cap 222 is between about 0.2 cm and about 0.5 cm.

Referring to FIGS. 3G to 3J, free end 204 of sleeve 202 preferably is closed using a cap 222. Cap 222 is coupled to sleeve 202 by first placing cap 222 with wide portion 232 of locking portion 228 centrally disposed within free end 204 of sleeve 202 and narrow portion 230 of locking portion 228 disposed in slot 214 of sleeve 202. In this position, central line 233 of cap 222 is aligned with central line 240 extending along a diameter of sleeve 202, centrally through slot 214. With lip 236 of cap 222 disposed in groove 216 of sleeve 202, cap 222 is securely coupled to sleeve 202 by rotating cap 222 in the direction of arrow A, such that lines 233, 240 of cap 222 and sleeve 202, respectively, are no longer colinear. In some embodiments, groove 216 is interrupted to create a stop (not shown), as for example located at region 242, thereby preventing additional rotation of cap 222.

With a cap 222 installed on sleeve 202, plug 200 includes a chamber 244 with one end open. This chamber 244 may be packed with such materials as bone chips, slurries of bone particulate, bone fibers, bone-growth inducing substances, hydroxyapatite, polymers such as polymethylmethacrylate, ceramics, bone cement, or other materials. In a preferred embodiment, sleeve 202 and cap 222 are formed of cortical bone, and chamber 244 is packed with a cylinder 246 that is preferably formed of cancellous bone and inserted prior to installation of cap 222. Alternatively, other materials such as porous ceramics may be used. Holes 208 facilitate incorporation of plug 200 into surrounding bone tissue, by permitting ingrowth as well as access to materials retained in chamber 244. If a solid cylinder 246 having a diameter of about D, is inserted into chamber 244, the cylinder may be prevented from removal through free end 206 by a circumferential lip 245. Thus, an end cap is not required at free end 206 to retain cylinder 246. The cortical bone may be obtained from the thin cortical bone proximate the ends of long bones, such as the humerus or tibia, or other regions. A sleeve 202 and cap 222 formed of cortical bone provide structural integrity to plug 200, and advantageously the cortical bone is readily machinable to repeatable dimensions and desirable tolerances. In an alternate embodiment, cylinder 246 may be formed of a main cancellous body portion 248 and a cortical end cap 250, with cortical end cap 250 disposed in a free end of sleeve 202 such that both free ends are closed by cortical bone for added structural integrity. In another alternate embodiment, cylinder 246 may be used as a plug. Although cylinder 246 is shown as a one-piece component, cylinder 246 alternately may be formed of two or more portions, for example, by sectioning cylinder 246 along lines 247, 248. A sectioned cylinder 246 may loosely fit in a sleeve, with the sectioning permitting expansion of the cylinder portions or contraction of the sleeve without creating significant stress on the components.

When plug 200 is inserted into an anatomical vacancy, preferably open free end 206 is inserted first such that cortical cap 222 faces outward. Other materials may be used to form plug 200, such as metals or ceramics. To facilitate insertion of plug 200, the circumferential edge 252 proximate free end 206 preferably is chamfered to assist in guiding plug 200 into the vacancy.

In an alternate embodiment, a plug 260 includes a cylindrical, cortical shell 262 and a filler 264. Preferably, filler 264 is harvested from a femoral head, and thus naturally includes integral cancellous and cortical bone portions 266, 268, respectively. The natural geometry of cortical bone portion 268 is curved or otherwise variable at free end 270, and a flat free end 270 is not necessary to provide sufficient structural integrity. In one embodiment, filler 264 may be harvested from a femoral head, although it is difficult to obtain a natural, uniformly thick cortical bone portion 268. Preferably, the distance $L_3$ from a free end of cortical shell 262 to a hole 272 is chosen so that cortical bone portion 268 does not intersect any holes 272, and filler 264 may then prevent the release of blood or other fluids from within the plug or vacancy in which it is inserted. Optionally, a cortical cap may be disposed proximate free end 270; cortical bone portion 268 of filler 264 may serve as a redundant cortical sealing for plug 260 should the cap become detached.

Another alternate embodiment of a plug 280 includes a shell or sleeve 282 with holes 284 and threading 286 on outer surface 288. Plug 280 is thus configured to be threadably received in an anatomical vacancy in bone tissue. Threading on the inner surface of plug 280 also may be provided.

Figure 4A:
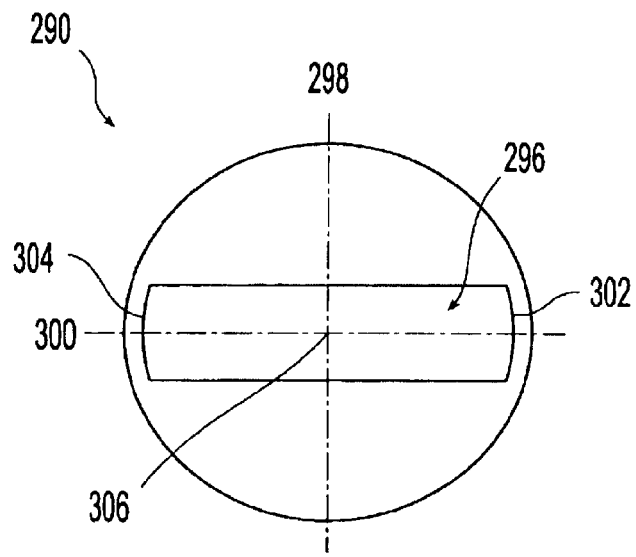
FIGS. 4A to 4C show a top view, side view, and another side view, respectively, of an additional embodiment of a cap according to the present invention.
Figure 4B:
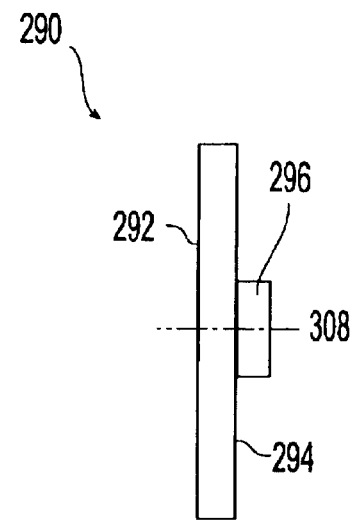
Figure 4C:
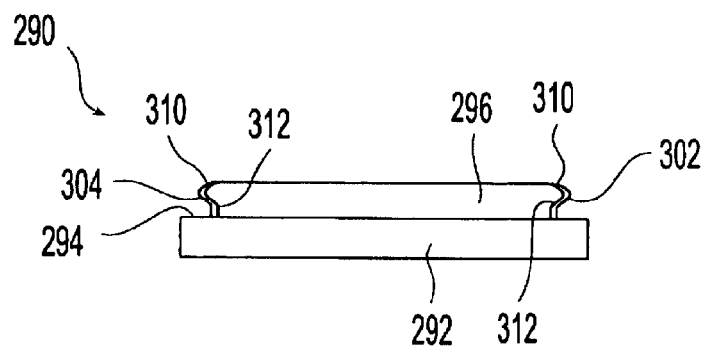
Figure 4D:
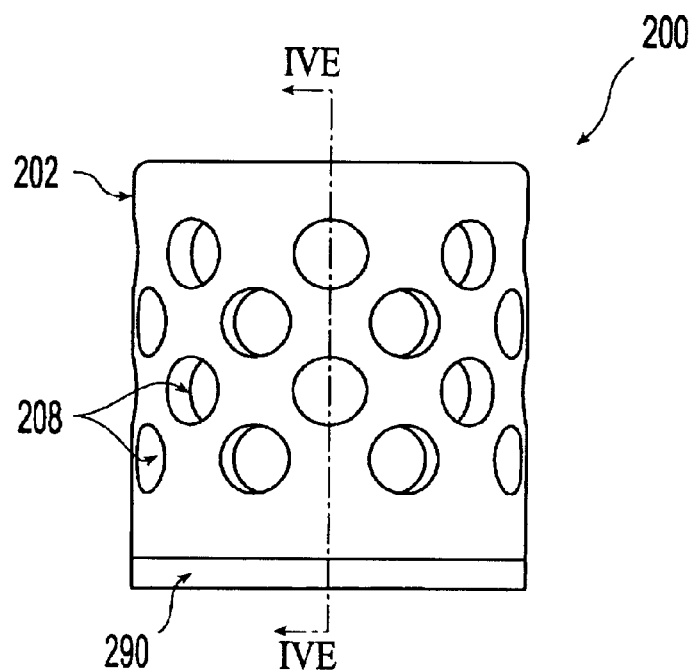
FIG. 4D shows a side view of the cap of FIG. 4A installed in a sleeve of a plug according to the present invention.
Figure 4E:
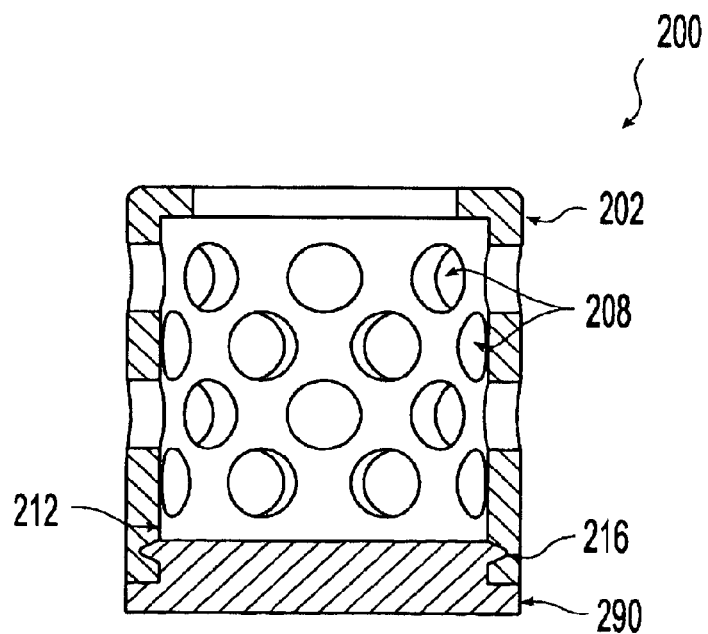
FIG. 4E shows a cross-section of the cap of FIG. 4A through line IVE—IVE.
Figure 4F:
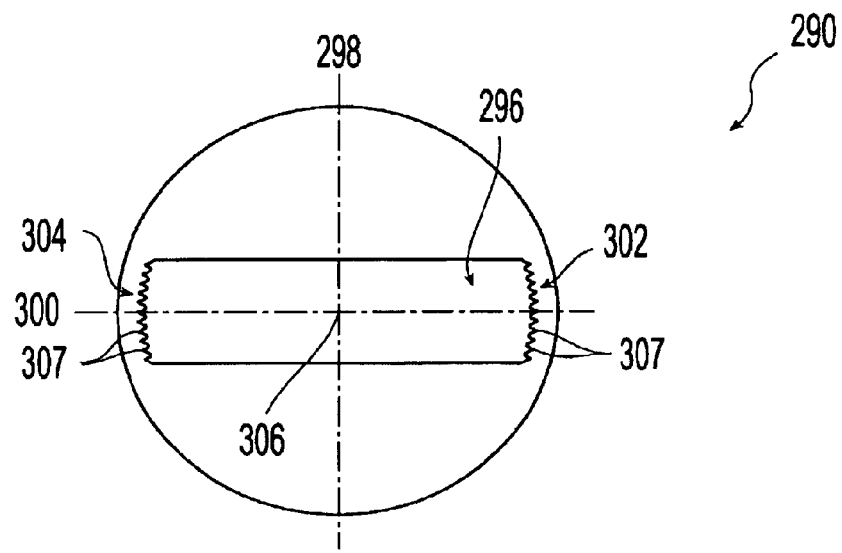
FIG. 4F shows a bottom view of a cap with a locking portion having serrated edges according to the present invention.

Another embodiment of a cortical cap suitable for the present invention is shown initially in FIGS. 4A to 4C. Cap 290 includes a top surface 292 and a bottom surface 294. A locking portion 296 preferably is integrally formed on bottom surface 294, and is symmetrical about central lines 298, 300. The outer edges 302, 304 of locking portion 296 are preferably disposed along the circumference of a circle centered about point 306 along central axis 308 of cap 290. As shown in FIG. 4C, locking portion 296 of cap 290 includes a lip 310 and a wall 312. As discussed with respect to cap 222, lip 310 of cap 290 is sized to fit and turn within groove 216 in sleeve 202, while wall 312 is sized to fit and turn proximate inner surface 212 of sleeve 202. A cap 290 may be coupled to a sleeve 202, preferably by snap-fitting of lip 310 of cap 290 in groove 216 of sleeve 202, as shown in FIGS. 4D and 4E. The snap-fitting of cap 290 to sleeve 202 obviates the need for a slot 214 in sleeve 202. The hole pattern of sleeve 202 may be varied, and different hole patterns are shown in FIGS. 3A and 4D. Alternate embodiments of cap 290 may include serrations, ribbing, scoring, or other undulating features on edges 302, 304 of locking portion 296, such as ribs 307 shown in FIG. 4F.

Alternatively, such ribs may be oriented in a plane perpendicular to line 308, following the curvature of edges 302, 304, as shown in FIG. 4B. Ribs 307 may be used to lower tolerances between edges 302, 304 and receiving surfaces on a sleeve. Additionally, the grooving in a sleeve for receives edges 302, 304 may be provided with similar undulating features for positive interlocking.

Figure 4G:
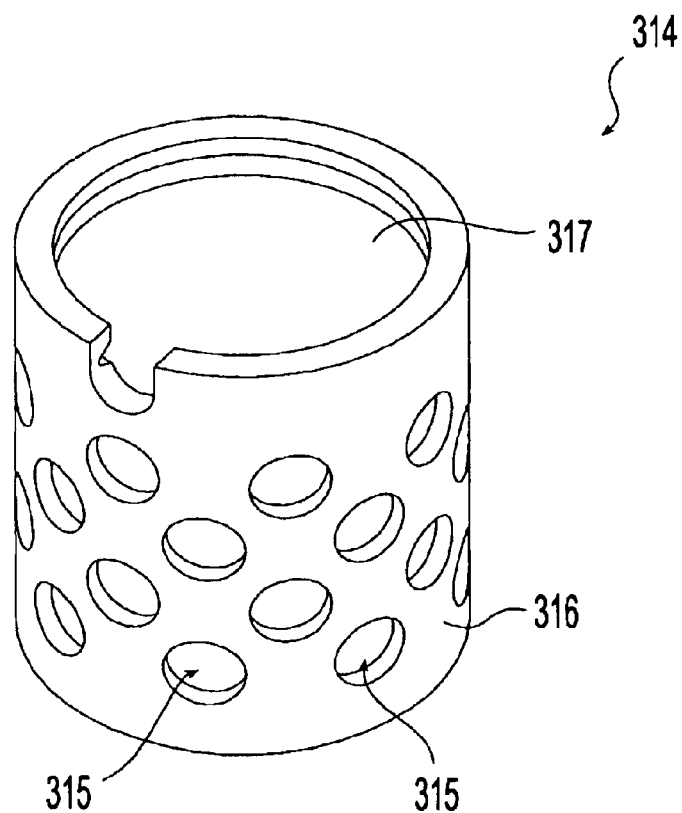
FIG. 4G shows a perspective view of a sleeve with recesses on the outer surface for a plug formed according to the present invention.

An alternate sleeve 314 for use in a plug is shown in FIG. 4G. Sleeve 314 includes recesses 315 formed in outer surface 316. Recesses 315 do not extend through inner surface 317. Although recesses 316 are shown in the shape of circular depressions, the recesses may be other shapes such as dimples formed from a spherical geometry, diamond shapes, or rectangular shapes.

Figure 5D:
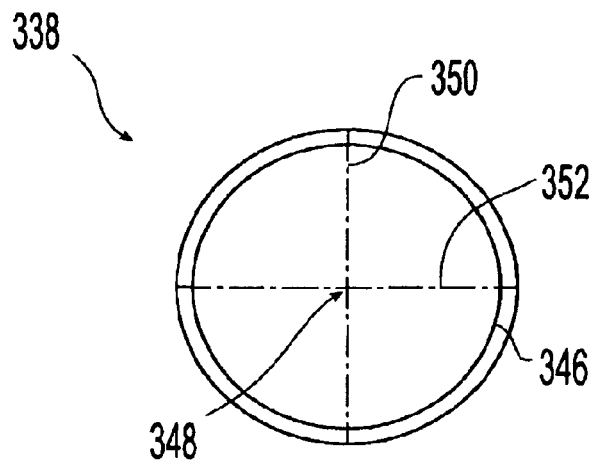
FIGS. 5D and 5E show top and side views, respectively, of an additional embodiment of a cap for a plug according to the present invention.
Figure 5E:
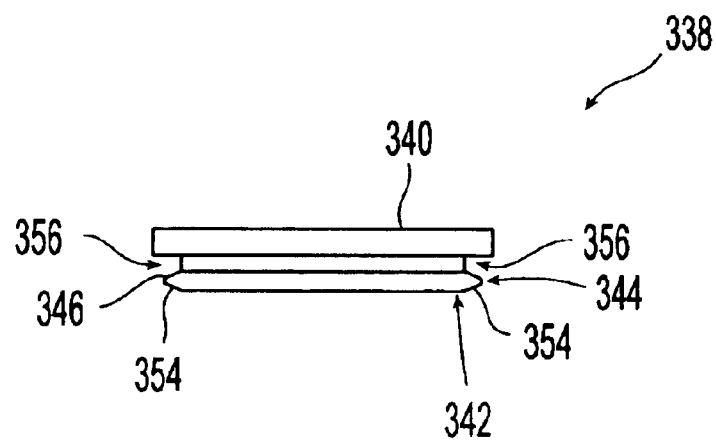

A further embodiment of a plug is shown in FIGS. 5A to 5C. Plug 320 includes a sleeve 322 with holes 324 and elongate slots 326 extending from free end 328 toward free end 330. Due to the positioning of slots 326, fingers 327 are formed. Advantageously, fingers 327 provide flexibility at free end 328, thus facilitating the snap-fitting of a cap on free end 328. Preferably, holes 324 are disposed in aligned groups, such as along line 332. A circumferential groove 334 is provided to facilitate coupling of a cap to sleeve 322, as discussed previously. Preferably, holes 324 and grooves 326 are disposed at a generally constant angular interval $\theta_2$ with respect to each other, as measured from the center of sleeve 322 at point 336. Preferably, angle $\theta_2$ is between about 35° and about 55° and more preferably about 45°. Another cap particularly suitable for use with plug 320 is cap 338, shown in FIGS. 5D and 5E. Cap 338 includes a top surface 340 and a bottom surface 342. A locking portion 344 preferably is integrally formed on bottom surface 342, and is circular. The outer edge 346 of locking portion 344 is disposed along the circumference of a circle centered about point 348, formed at the intersection of diameters 350, 352. Referring to FIG. 5E, locking portion 344 of cap 338 includes a lip 354 and a wall 356. As discussed with respect to other embodiments of caps, lip 354 of cap 338 is sized to fit within groove 334 in sleeve 322, while wall 356 is sized to fit proximate the inner surface of sleeve 322.

Caps referred to herein may be coupled to sleeves using a variety of other structures, including threading, ribs, teeth, tapers, and knurled surfaces. In addition, the use of adhesive bonding is also contemplated.

Although circular, elongate, and irregular protrusions have been disclosed for use in coupling caps to sleeves, other configurations of protrusions are also contemplated for use in the present invention. For example a protrusion with a triangular or rectangular geometry may be used to provide three or four points of contact, respectively, with the inner walls of a sleeve. A cross-shaped protrusion would also provide four regions of contact. In one embodiment, a rectangular protrusion is provided with a length that is a factor of three greater than the width.

Figure 6A:
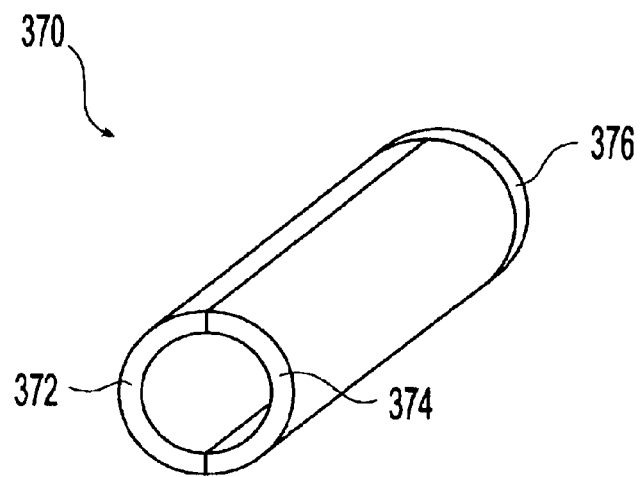
FIG. 6A shows a perspective view of an additional embodiment of a plug according to the present invention.
Figure 6B:
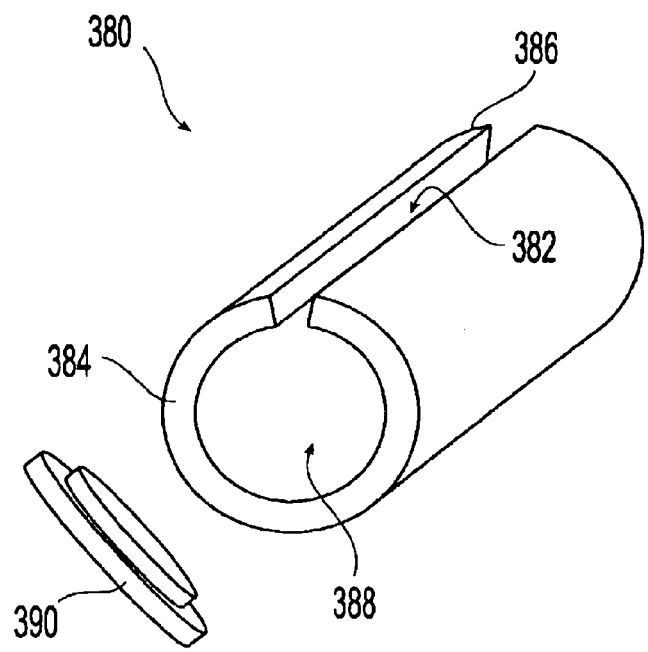
FIG. 6B shows an exploded, perspective view of another embodiment of a plug according to the present invention.

With respect to sleeve constructions, multipiece sleeves are also contemplated. For example, as shown in FIG. 6A, a sleeve 370 may be formed from two portions of bone 372, 374 that are interfitted together and closed at one end using a cap 376. Another sleeve 380 is shown in FIG. 6B, and includes a slit 382 extending from free end 384 to free end 386. Slit 382 is sized such that when a cylindrical filler is inserted into hollow region 388, sleeve 380 is permitted to flex to accommodate dimensional differences between the inner diameter of sleeve 380 and the outer diameter of the filler. Ends 384, 386 may be closed using caps, as discussed previously, for example with a cap 390. Cap 390 may optionally be provided with a slit extending from a central point to the outer diameter of the cap. Sleeve 380 also may be compressed when inserted in a vacancy, such as in a vertebral body; after insertion, sleeve 380 may re-expand to more closely fit against the walls of the vacancy. Also, sleeve 380 may be inserted into a vacancy and expanded using a wedge or pin that is subsequently inserted into slit 382.

Figure 7A:
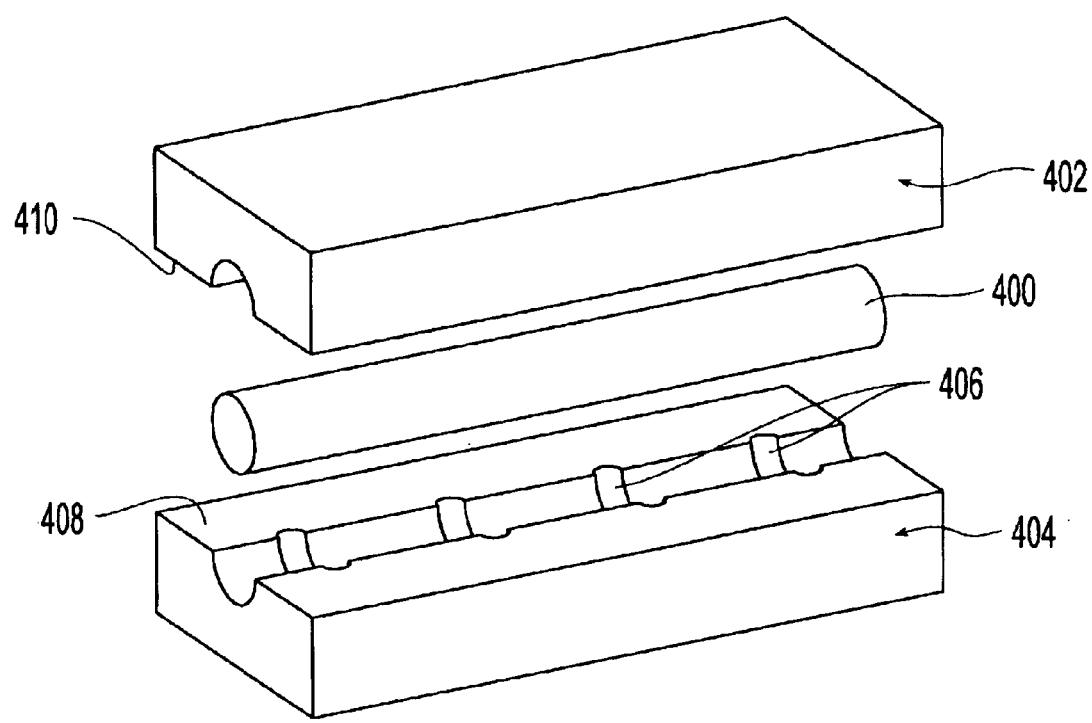
FIGS. 7A and 7B show the forming of a cancellous plug between a pair of dies according to the present invention.
Figure 7B:
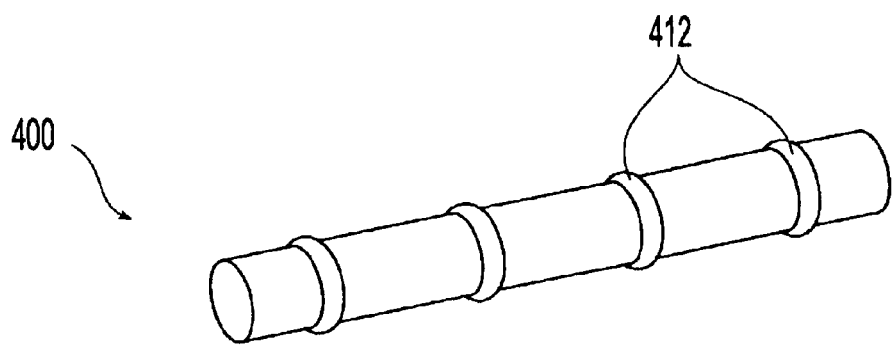

With respect to cancellous fillers for sleeves, or plugs formed of cancellous bone, the cancellous bone may be shaped to a desired geometry using dies, as shown in FIGS. 7A and 7B. Such a manufacturing process provides an alternative to turning or milling, which may be more difficult than pressing for cancellous bone. A section of cancellous bone 400 is disposed between a pair of dies 402, 404, which may include particular geometrical features such as indentations 406, protrusions, or other shapes. Once dies 402, 404 are brought together such that surfaces 408, 410 contact each other, an oversized bone section 400 is compressed and molded into the geometry of the dies. As shown in FIG. 7B, compression of a bone section 400 that is initially smooth and cylindrical in dies 402, 404 results in the formation of ribs 412 about the circumference of bone section 400 due to the compression of portions of bone section 400 in indentations 406. Thus, machining of such cancellous bone fillers may be avoided.

Advantageously, plugs formed of cancellous bone may be attached to syringes or aspirators, and blood or other fluids such as bone-growth inducing substances may be drawn into the plugs. The use of mechanically applied pressure, such as with aspiration devices, permits a greater degree of fluid absorption and/or concentration to be achieved than otherwise readily obtainable by soaking bone in such fluids without applying pressure from a device. In embodiments of the present invention that include hollow regions, a bone component of cancellous bone formed using the aforementioned technique maybe inserted therein.

Other embodiments of plugs according to the present invention in the form of dowels are shown in FIGS. 8 to 15. Plugs described and depicted as sleeves alternatively may be formed as solid plugs with the outer contours shown in the figures. In the preferred embodiments, the plugs are generally cylindrical. Turning to FIG. 8A, a plug 500 includes a sleeve or solid portion 510 formed of a single piece of bone. Grooved regions 504 are provided proximate free end 506, and preferably include angled edges 510 disposed at an angle $\theta_3$ with respect to outer surface 512. Preferably, angle $\theta_3$ is between about 20° and about 40°, and more preferably about 30°. Preferably, plug 500 has an overall length $L_3$ of between about 1.7 cm to about 2.3 cm, and more preferably about 2.0 cm, while the outer diameter $D_5$ is between about 1.4 cm and about 1.8 cm, and more preferably about 1.6 cm. In one embodiment, plug 500 is formed from bone harvested from a condyle. Thus, bone proximate free end 508 may be cortical, while the remainder of plug 500 is formed of cancellous bone. As shown in the side view of FIG. 8B, free end 506 of sleeve portion 510 has a circular wall 514 with a chamfer 511 to facilitate insertion of plug 500 into a vacancy. Similarly, a plug 520 shown in FIGS. 9A and 9B is formed of a sleeve or solid portion 522 with flutes 524 disposed about the outer surface 526 of portion 522 proximate a free end 528, as partially indicated in phantom. If plugs 500, 520 are formed as sleeves, central chambers 516, 529, respectively are formed therein. Additional forms of fluting for similarly dimensioned plugs are shown in FIGS. 10 to 11. Plugs 530, 540 include flutes 532, 542 respectively. Side views from ends 534, 544 of plugs 530, 540, respectively, are shown in FIGS. 10B and 11B.

Further embodiments of plugs according to the present invention are contemplated. Plug 550, shown in side view in FIG. 12, includes a sleeve 552 with a chamfered end 554. As shown in FIG. 13 in cross-section, a generally cylindrical plug 560 includes cortical end caps 562, 564 disposed at the ends of a cancellous sleeve 566. End cap 564 includes chamfered edges 568. A central chamber 570 is also formed, and may be filled with a cylindrical element 572 formed of cortical bone in the shape of a pin to improve structural integrity. Preferably, element 572 is press-fit within sleeve 566 and end caps 562, 564. Similarly, as shown in FIGS. 14A and 14B, plug 580 includes an oversized end cap 582, while shown in FIGS. 15A and 15B is a plug 590 with an oversized end cap 592. The components of plugs 560, 580, 590 may be may be held together using ribbing, keys, pins, or other features as described previously with respect to other embodiments.

Additional embodiments of generally cylindrical plugs according to the present invention are shown in cross-section in FIGS. 16–25. Turning to FIG. 16, plug 600 includes a cortical sleeve 602 with through-holes 604, cortical end caps 606, 608, and a chamber 609 with a cancellous central filler 610 disposed therein. In an alternate embodiment, because end caps 606, 608 create a chamber 609, plug 600 may be filled with other materials such as bone chips. End caps 606, 608 may be press-fit or snapped within sleeve 602. Plug 620, as shown in FIG. 17, includes a cortical cap 622 and a cancellous body 624, which together form a central, substantially right cylindrical chamber 626. Plug 630, shown in FIG. 18, includes a cortical cap 632 with a central through-hole 634, aligned with a cancellous sleeve 636 with a central through-hole 638. Holes 634, 638 are aligned such that a suitably sized pin 639 extends therethrough. In some embodiments, holes 634, 638 form a tapered hole such that a generally frustoconical chamber is formed for receiving a like-shaped filler such as a cancellous bone filler.

As shown in FIG. 19, a plug 640 includes a cortical sleeve 642 with a substantially right cylindrical cancellous insert 644; sleeve 642 is closed at one end with a cortical end cap 646. Plug 650 includes a cortical end cap 652 that is threadably received in a cancellous body 654. A chamfer 656 is provided at face 658, opposite end cap 652, to assist in guiding the insertion of plug 650 into a vacancy. A plug 660 includes a cortical end cap 662 and a cancellous body 664. A cortical insert 666 extends through end cap 552 and partway through body 664. Insert 666 is fixed to body 664 with a pin 668 which extends through body 664 and insert 666. Pin 668 is shown extending generally perpendicular to the plane of the page. In the embodiment shown in FIG. 22, plug 670 includes a cap 672 that press fits to sleeve 674 along both the outer and inner surfaces 676, 678, respectively. Optionally cap 672 may be pinned in place with a pin 679 extending through both cap 672 and sleeve 674. Additionally, as shown in FIG. 23, a plug 680 includes a cortical cap 682 that is locked within sleeve 684 by a cancellous insert 686. Components 682, 686 may instead be integral, formed for example by machining a potion of bone harvested from a femoral head, as described previously with respect to plug 260. A pin 688 further constrains movement of cancellous insert 686. In yet another embodiment, a sleeve 692 of plug 690 is provided with a dovetail-shaped through-slot 694 at one end so that a cap 696 may be coupled to sleeve 692 by sliding dovetail portion 698 within slot 694 from either end of the slot. Also, a plug 700 may be formed by press-fitting or loosely fitting a cortical cap 702 to a cancellous body 704 and further coupling cap 702 to body 704 with a pin 706 as shown in FIG. 25.

Turning to FIG. 26, plug 710 includes a body 712 with a protrusion 714 having slots 716. When a cap 718 with a central hole 720 is placed around protrusion 714, the protrusion may contract so that the width of slots 716 decreases, thereby providing a tighter fit of cap 718 to an oversized protrusion 714.

Figure 27:
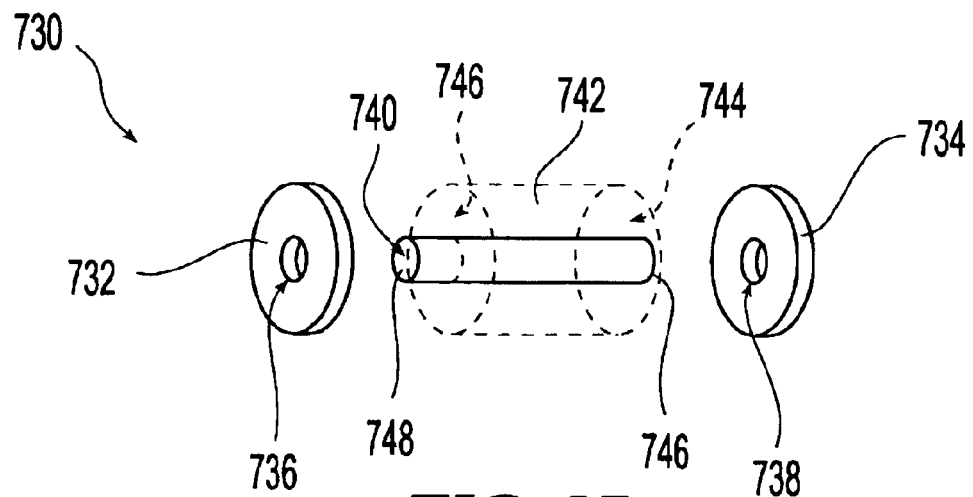
Figure 28:
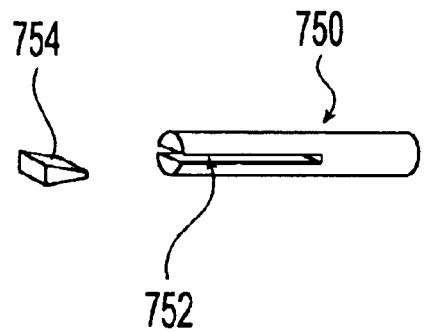
FIGS. 28 and 29 show perspective views of insertable components for use with plugs according to the present invention.
Figure 29:
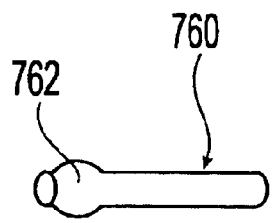

Another plug 730 according to the present invention is shown in exploded perspective view in FIG. 27. Washer-like end caps 732, 734 include central holes 736, 738, respectively, for receiving a central member 740. Preferably, end caps 732, 734 and central member 740 are formed of cortical bone. Member 740 also passes through a central hole in body 742, extending beyond each free end 744, 746 thereof, such that holes 736, 738 receive portions of member 740. Preferably, member 740 includes interlocking features at free ends 746, 748 to facilitate coupling. Such features may include a taper, ribs, threads, saw teeth, flanges, or knurls. In one embodiment, shown in exploded perspective view in FIG. 28, a member 750 suitable for use with plug 730 includes a slotted portion 752 and an insertable wedge-shaped portion 754. Rod 750 is initially disposed in an end cap hole such as hole 736, without wedge-shaped portion 754. Rod 750 is locked in place to end cap 732 by inserting wedge-shaped portion 754 in slot 752 and thus increasing the effective diameter of rod 750 so that a press-fit within hole 736 is achieved. Similarly, a press-fit may be achieved using a member 760 with a bulging end 762, as shown in the perspective view of FIG. 29. Insertion of bulging end 762 in a hole 736, for example, provides a fit such that member 760 may be coupled to end cap 732. Such a member 760 may be in the form of a button snap mechanical fastener.

Yet another plug 770 according to the present invention is shown in FIGS. 30A to 30D. As shown in the cross-sectional side view of FIG. 30A, plug 770 includes end cap 772, tapered sleeve 774, and tapered insert 776 sized to fit in sleeve 774. A pair of L-shaped recesses 776 are disposed proximate end 778, as shown in the perspective view of FIG. 30B. As shown in side view in FIG. 30C and bottom view in FIG. 30D, end cap 772 includes head 780 and shaft 782. A pair of opposing protrusions 784 are disposed on shaft 782. Protrusions 784 are located and sized on shaft 782 such that end cap 772 may be inserted onto end 778 of sleeve 774 with protrusions 784 fitting in L-shaped recesses 776. To fix end cap 772 to sleeve 774, end cap 772 is turned so that protrusions 784 abut edges 786 of recesses 776.

Figure 31A:
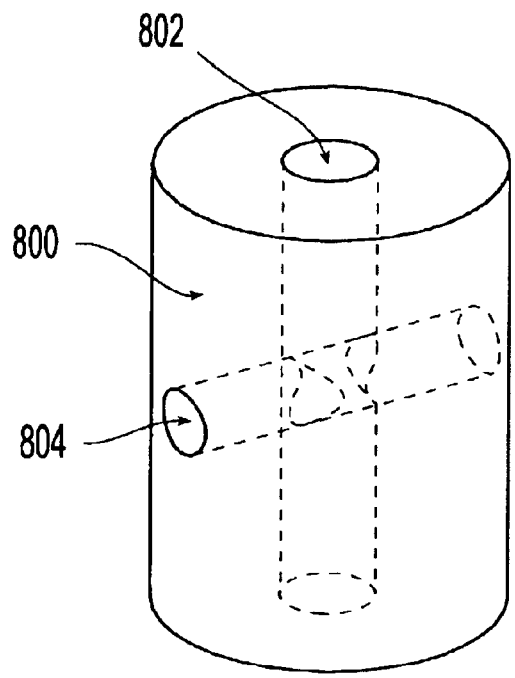
FIGS. 31A and 31B show the formation of a plug from a cross-section of a bone taken transverse to the long axis of a bone.
Figure 31B:
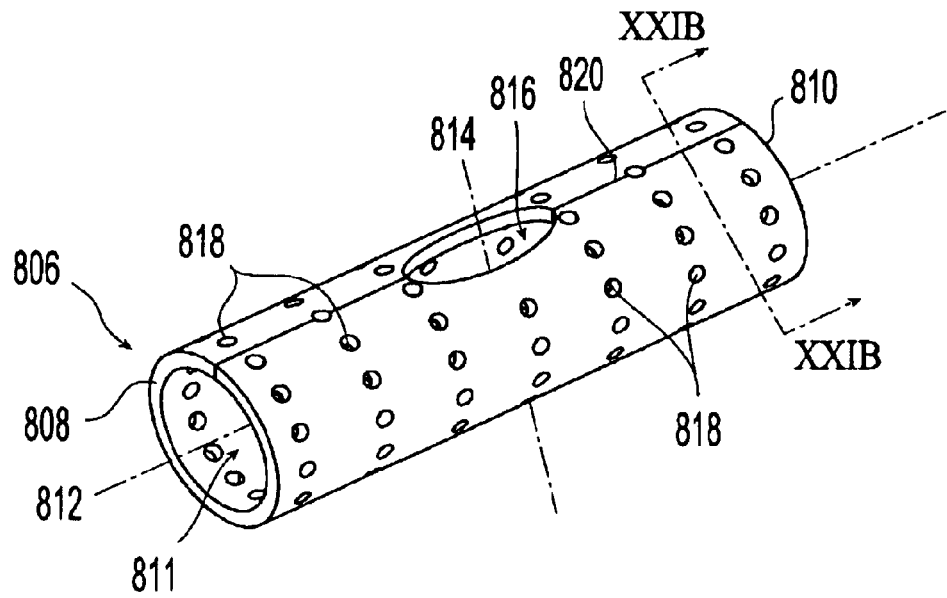

Referring now to FIG. 31A, a section 800 of a long bone such as a humerus is shown. Although the particular geometry of the inside and outside of the bone is shown as being generally cylindrical for exemplary purposes, a plug formed from section 800 in part may follow the natural outer and inner geometry of section 800. Bone 800 includes a canal 802. A generally cylindrical plug 804, taken transverse to the long axis of a bone, may be removed from bone section 800 and may be used to form a plug 806. Plug 806 includes free ends 808, 810. When initially removed from bone section 800, free ends 808, 810 are both closed. A cavity 811 may be bored into a free end 808, 810. Preferably, cavity 811 is disposed about axis 812, which is generally perpendicular to axis 814 of through-hole 816 formed by canal 802. Thus, cavity 811 is bounded by an open free end 808 and closed free end 810, forming a sleeve. Plug 806 may be filled with materials such as bone chips, bone particulate, bone fibers, bone growth materials, hydroxyapatite, metal, resorbable material, polymer, ceramic, and bone cement. Preferably, perforations 818 are formed in plug 806. A cap (not shown) also may be fixed to free end 808. Preferably, alignment indicia 820 is provided such as a line extending from free end 808 to free end 810 and across through-hole 816. Free end 810, which is closed, also may include indicia. Such indicia may facilitate positioning of plug 806 by a surgeon, particularly with respect to the orientation of through-hole 816 in the anatomical vacancy to be filled. In addition, it should be noted that a section taken through line XXIB—XXIB may create an end cap such as cap 718 shown in FIG. 26.

Figures 32A, 32B:
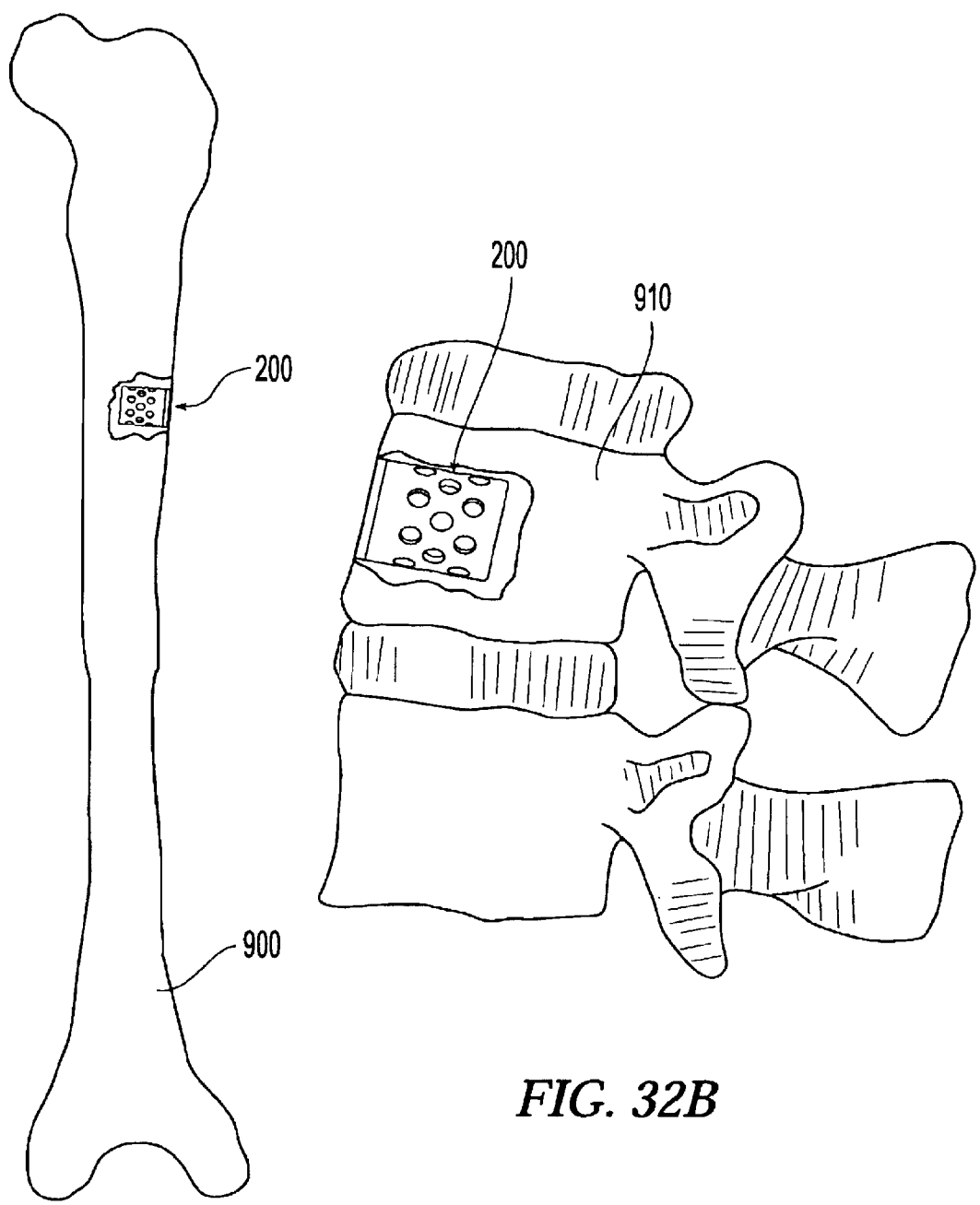
FIGS. 32A and 32B show partial cross-sections of a long bone and a vertebral body, respectively, with a bone plug inserted therein.

The plugs disclosed in the present invention may be sized to meet a particular need and applied in areas of bony tissue. Exemplary use of the plugs described herein is shown in FIGS. 32A and 32B. A plug 200, for example, may be used in a bone such as a long bone 900. In addition, a plug 200 may be used in a vertebral body 910. Plugs 200 are used to fill voids that may exist or be created in long bone 900 and vertebral body 910 due to trauma, disease, malformation, or other conditions. Also, the plugs may be used to fill holes in healthy bone tissue that are surgically created when healthy tissue is removed for transplantation to other bony regions of the body.

The embodiments of plugs disclosed herein may include components that are initially provided with a first moisture content, but then allowed to assume a new configuration with a second moisture content. For example, in the embodiment shown in FIG. 4E, a cap 290 is used with a sleeve 202. Cap 290 may have a first outer diameter for lip 310. Freeze-drying of cap 290 results in shrinkage such that lip 310 assumes a configuration with a second outer diameter that is smaller than the first outer diameter. When cap 290 is rehydrated or treated with a swelling agent, lip 310 of cap 290 may reassume a configuration with the first outer diameter. Plug 200 initially may be provided with a freeze-dried cap 290 disposed inside another bone section such as sleeve 202 so that a loose interference fit is achieved, and subsequent rehydration of cap 290 in place permits a tighter interference fit. Notably, the shrinkage and expansion effects may be used with bone components that have both outer and inner diameters, such as sleeve 202.

For example, sleeve 202 initially may be supplied with a first outer diameter and a first inner diameter, and subsequently freeze-dried so that sleeve 202 assumes a configuration with a second outer diameter that is smaller than the first outer diameter, while having a second inner diameter that is smaller than the first inner diameter. When sleeve 202 is rehydrated or treated with a swelling agent, sleeve 202 may reassume a configuration with the first outer diameter and a first inner diameter. Thus, sleeve 202 may first be provided in dehydrated state to loosely fit in a void, and rehydrated after insertion to provide a tighter interference fit between the sleeve and its anatomical surroundings. Use of these properties also can permit greater variation in dimensional tolerance between bone sections during manufacture, while tight final assembly can still be achieved. In addition, protrusions on bone sections become smaller when dehydrated, but expand when rehydrated; in contrast, recesses in bone sections become smaller when hydrated, but larger when dehydrated. Furthermore, temperature changes may be used to achieve better interference fits.

Figure 3N:
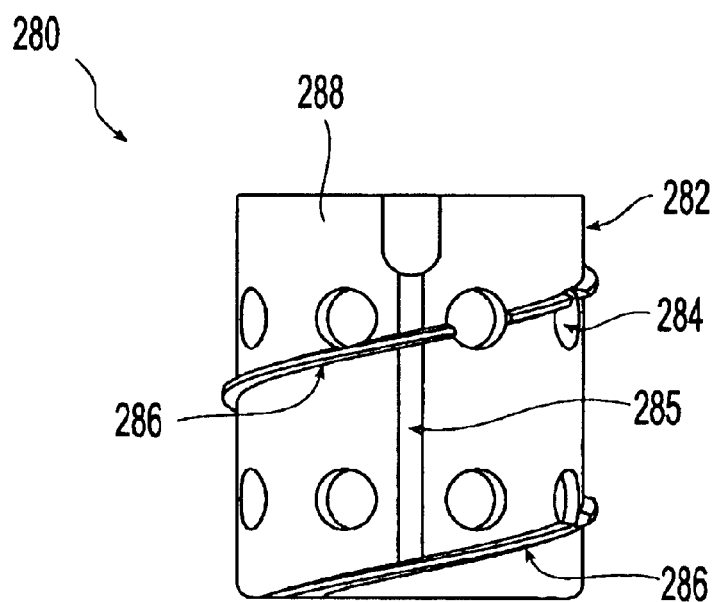
FIG. 3N shows another embodiment of a sleeve for a plug according to the present invention with threading.

Alignment indicia 285 such as a line along the side of sleeve 280, as shown in FIG. 3N, may be provided on the outer surface of the sleeve. Preferably, indicia 285 is an imprint, i.e. with ink, although indicia 285 may instead be provided in the form of surface scoring or a protrusion on the surface. In addition to sleeves, caps may also be provided with indicia to assist in properly orienting the caps, along with any component coupled thereto, after insertion into an anatomical void. Also, the indicia may be used to properly align a plug with a particular body or sleeve hole configuration to facilitate and guide the release or exposure of substances contained therein. The indicia suitable for the present invention includes, but is not limited to, markers such as lines, arrows, lettering, and symbols.

Numerous types of joints are useful in the present development, including joints that permit articulation such as a ball and socket type of joint, and particularly joints that permit firm interlocking between two components to prevent relative movement between the components. Preferably, mortise and tenon joints can be used to interfit components of the plugs. Other coupling arrangements such as edge joints including tongue and groove joints, rabbeted joints, toothed joints, and dovetail joints are also suitable for the present invention.

The use of insertable securing elements such as keys, pegs, pins, wedges, or other suitable components in joints to assist in securing bone components to each other is also an effective approach to providing a stable joint. Keys, for example, may be inserted in notched or grooved areas in plug components, serving as the securing element between two or more plug components. Parameters that may be varied when using insertable securing elements, such as keys, include the angle of application, the spacing of the elements, and the thicknesses of the elements.

While various descriptions of the present invention are described above, it should be understood that the various features can be used singly or in any combination thereof. The various types of joints and connections can be used on plugs of different size or configuration, such that the invention is not to be limited to only the specifically preferred embodiments depicted in the drawings.

Further, it should be understood that variations and modifications within the spirit and scope of the invention may occur to those skilled in the art to which the invention pertains. For example, multiple, differently shaped and sized plugs can be constructed for interfitting or interconnection to form a multiple part plug that serves the desired purpose. Accordingly, all expedient modifications readily attainable by one versed in the art from the disclosure set forth herein are within the scope and spirit of the present invention and are to be included as further embodiments. The scope of the present invention is accordingly defined as set forth in the appended claims.

What is claimed is:

1. A plug for filling a vacant region in anatomical bone, comprising:
   a body with a top end, a bottom end, and an outer surface disposed between the top and bottom ends; and
   a first cap comprising a locking portion mechanically lockable to an end of the body and configured and dimensioned to be rotatably received in the body,
   wherein the locking portion extends substantially across a face of the first cap, and
   wherein the body and first cap are substantially formed from bone selected from the group consisting of cortical and cancellous bone.

2. The plug of claim 1, wherein the body comprises a sleeve with an inner surface.

3. The plug of claim 2, further comprising an insert configured and dimensioned to be received in the sleeve.

4. The plug of claim 3, wherein the insert is formed of cancellous bone.

5. The plug of claim 4, wherein the cancellous bone has a fluid concentrated therein.

6. The plug of claim 5, wherein the insert is subjected to mechanical pressure to concentrate the fluid.

7. The plug of claim 6, wherein the mechanical pressure is applied by aspiration.

8. The plug of claim 5, wherein the fluid is concentrated by soaking.

9. The plug of claim 4, wherein the insert is secured to at least one of the sleeve and first cap with at least one fastener.

10. The plug of claim 9, wherein the at least one fastener is selected from a screw, key, pin, peg, rivet, cotter, nail, spike, bolt, stud, staple, boss, clamp, clip, dowel, stake, hook, anchor, tie, band, crimp, and wedge.

11. The plug of claim 10, wherein at least one of the sleeve, first cap, insert, and fastener is formed from partially demineralized or demineralized bone.

12. The plug of claim 9, wherein at least two of the sleeve, first cap, insert, and fastener are bonded together with a bonding agent.

13. The plug of claim 9, wherein at least one of the sleeve, first cap, insert, and fastener is at least partially dehydrated to loosely fit within a surrounding mating surface.

14. The plug of claim 4, wherein at least one of the sleeve, first cap, and insert further comprises alignment indicia.

15. The plug of claim 2, wherein the sleeve is packed with at least one of bone chips, bone particulate, bone fibers, bone growth materials, hydroxyapatite, metal, resorbable material, polymer, ceramic, and bone cement.

16. The plug of claim 15, wherein the sleeve further comprises at least one through-hole extending from the inner surface to the outer surface.

17. The plug of claim 16, wherein the sleeve is cylindrical.

18. The plug of claim 15, wherein the sleeve further comprises at least one depression extending from the outer surface toward the inner surface.

19. The plug of claim 2, wherein the sleeve further comprises a plurality of fingers formed integrally therewith.

20. The plug of claim 2, wherein the sleeve and first cap are substantially formed of cortical bone.

21. The plug of claim 2, wherein the body is formed of cancellous bone and the first cap is formed of cortical bone.

22. The plug of claim 2, wherein one of the top and bottom ends of the body is open.

23. The plug of claim 1, further comprising a second cap disposed on a different end from the first cap.

24. A plug for filling a vacant region in anatomical bone, comprising
   a sleeve comprising a top end, a bottom end, an inner surface, an outer surface disposed between the top and bottom ends, a groove disposed on the inner surface proximate one of the ends, and a plurality of through-holes extending from the inner surface to the outer surface; and
   a first cap comprising opposing faces and a locking portion configured and dimensioned to be received in the groove;
   wherein one of the faces of the first cap abuts one of the ends of the sleeve, and
   wherein the sleeve and first cap are substantially formed of bone.

25. The plug of claim 24, wherein the sleeve and first cap are substantially formed of cortical bone.

26. The plug of claim 24, wherein the sleeve is formed of cancellous bone and the first cap is formed of cortical bone.

27. The plug of claim 24, wherein one of the top and bottom ends of the body is open.

28. The plug of claim 24, wherein the sleeve further comprises threading disposed on the outer surface thereof.

29. The plug of claim 24, wherein the sleeve further comprises a slot intersecting the groove.

30. The plug of claim 29, wherein the slot has a width sized to allow passage of a portion of the locking portion of the cap.

31. The plug of claim 24, wherein the outer surface of the sleeve is substantially cylindrical.

32. The plug of claim 24, wherein the outer surface of the sleeve is substantially arcuate.

33. The plug of claim 29, wherein the sleeve further comprises a central axis and a circumferential lip extending toward the central axis.

34. The plug of claim 33, wherein the circumferential lip is disposed proximate an end of the sleeve.

35. The plug of claim 24, wherein the sleeve further comprises a chamfer proximate an end of the sleeve.

36. The plug of claim 24, wherein the locking portion is integrally formed the first cap.

37. The plug of claim 24, wherein the locking portion comprises a substantially arcuate outer edge.

38. The plug of claim 24, wherein the locking portion comprises a substantially circular outer edge.

39. The plug of claim 24, wherein the locking portion comprises an outer edge provided with undulations.

40. The plug of claim 39, wherein the undulations form a serrated edge.

41. The plug of claim 24, wherein the locking portion is generally symmetrical about a central line and tapers from a wide portion to a narrow portion.

42. The plug of claim 41, wherein the locking portion tapers from the wide portion to the narrow portion along a radius of curvature of between about 0.5 cm and 1.1 cm.

43. The plug of claim 41, wherein outer edges of the narrow and wide portions are disposed substantially along the circumference of a circle.

44. The plug of claim 24, wherein the locking portion is disposed on one of the faces of the first cap.

45. The plug of claim 24, wherein the first cap further comprises a first outer diameter and the sleeve further comprises a second outer diameter, the first and second outer diameters being about the same.

46. The plug of claim 24, wherein the sleeve further comprises a plurality of fingers formed integrally therewith.

47. The plug of claim 24, further comprising a second cap disposed on a different end from the first cap.

48. The plug of claim 24, wherein the sleeve further comprises a stop for limiting rotation of the locking portion of the first cap when disposed in the groove.

49. The plug of claim 48, wherein the stop interrupts the groove.

50. The plug of claim 24, wherein the groove extends circumferentially around the inner surface of the sleeve.

51. The plug of claim 24, further comprising an insert formed of bone and configured and dimensioned to be received in the sleeve.

52. The plug of claim 24, wherein the through-holes are arranged plurality of rows.

53. The plug of claim 52, wherein the rows are disposed in generally parallel planes.

54. The plug of claim 52, wherein the through-holes are disposed at a generally constant angular interval with respect to each other as measured from a central axis of the sleeve.

55. A plug for filling a vacant region in anatomical bone, comprising:
   a sleeve comprising a top end, a bottom end, an inner surface, an outer surface disposed between the top and bottom ends, a groove disposed on the inner surface proximate one of the ends, and a plurality of through-holes extending from the inner surface to the outer surface; and
   a first cap comprising opposing faces and a locking portion protruding from and extending substantially-across one of the faces, the locking portion being configured and dimensioned to be received in the groove;
   wherein the sleeve and first cap are substantially formed of bone.

* * * * *